US012697040B2

(12) United States Patent (10) Patent No.: US 12,697,040 B2
Shigehisa (45) Date of Patent: Aug. 4, 2026

(54) INSERTION ASSISTANCE SYSTEM, INSERTION ASSISTANCE METHOD, AND RECORDING MEDIUM

(71) Applicant: Evident Corporation, Nagano (JP)

(72) Inventor: Yoshiyuki Shigehisa, Fuchu (JP)

(73) Assignee: Evident Corporation, Nagano (JP)

( * ) Notice: Subject to any disclaimer, the term of this patent is extended or adjusted under 35 U.S.C. 154(b) by 790 days.

(21) Appl. No.: 17/843,037

(22) Filed: Jun. 17, 2022

(65) Prior Publication Data

US 2023/0030432 A1 Feb. 2, 2023

(30) Foreign Application Priority Data

Jul. 28, 2021 (JP) ................................. 2021-123407

(51) Int. Cl.
| | |
|---|---|
| *A61B 1/005* | (2006.01) |
| *A61B 1/00* | (2006.01) |
| *A61B 1/01* | (2006.01) |
| *A61B 1/04* | (2006.01) |
| *A61B 5/06* | (2006.01) |

(52) U.S. Cl.
CPC ................ *A61B 5/06* (2013.01); *A61B 1/005* (2013.01); *A61B 1/04* (2013.01); *A61B 1/0016* (2013.01); *A61B 1/01* (2013.01)

(58) Field of Classification Search
CPC ......... A61B 5/06; A61B 1/00; A61B 1/00004; A61B 1/00006; A61B 1/000096; A61B 1/005; A61B 1/0051; A61B 1/01; A61B 1/045
See application file for complete search history.

(56) References Cited

U.S. PATENT DOCUMENTS

| | | | | |
|---|---|---|---|---|
| 11,911,111 B2 * | 2/2024 | Konh | ................. | A61B 17/3478 |
| 2006/0173289 A1 * | 8/2006 | Aizawa | ................. | A61B 1/009 |
| | | | | 600/434 |
| 2019/0365479 A1 * | 12/2019 | Rafii-Tari | ............... | A61G 13/02 |

(Continued)

FOREIGN PATENT DOCUMENTS

| | | |
|---|---|---|
| CN | 103561628 A | 2/2014 |
| JP | 2002238839 A | 8/2002 |

(Continued)

OTHER PUBLICATIONS

Japanese Office Action dated Jan. 28, 2025 received in 2021-123407.

*Primary Examiner* — Michael J Carey
*Assistant Examiner* — William B Chou
(74) *Attorney, Agent, or Firm* — K&L Gates LLP

(57) ABSTRACT

An insertion assistance system includes a processor. The processor is configured to set a first position and a second position in shape information. The processor is configured to estimate a first state of a distal end of an insertion unit at the first position. The processor is configured to calculate a path through which the distal end passes. The processor is configured to determine a second state of the distal end at the second position. The processor is configured to output, to an information-reporting device, insertion assistance information required for an insertion operation for causing the distal end to reach the first position from the second position through the path and causing a state of the distal end to change from the second state to the first state.

13 Claims, 25 Drawing Sheets

(56)     References Cited

U.S. PATENT DOCUMENTS

| | | | | |
|---|---|---|---|---|
| 2022/0265969 A1* | 8/2022 | Pancaldi | ........... | A61M 25/0158 |
| 2023/0145309 A1* | 5/2023 | Wang | .................... | G16H 40/60 |
| | | | | 600/300 |

FOREIGN PATENT DOCUMENTS

| | | | |
|---|---|---|---|
| JP | 2004089483 | A | 3/2004 |
| JP | 2004187711 | A | 7/2004 |
| JP | 2005304937 | A | 11/2005 |
| JP | 4464640 | B2 | 5/2010 |
| JP | 5123615 | B2 | 1/2013 |
| JP | 2013240409 | A | 12/2013 |
| JP | 6030435 | B2 | 11/2016 |
| WO | 2003086498 | A2 | 10/2003 |
| WO | 2012101888 | A1 | 8/2012 |
| WO | 2014141968 | A1 | 9/2014 |
| WO | 2014156378 | A1 | 10/2014 |
| WO | 2014171391 | A1 | 10/2014 |

* cited by examiner

| BRANCH STATE | BRANCH PORTION |
|---|---|
| | BR10 |
| 1 | DR11 |

| BRANCH STATE | BRANCH PORTION | |
|---|---|---|
| | BR10 | BR11 |
| 1 | DR11 | DR12 |

| BRANCH STATE | BRANCH PORTION | |
|---|---|---|
| | BR10 | BR11 |
| 1 | DR11 | DR12 |
| 2 | DR12 | – |

| BRANCH STATE | BRANCH PORTION | |
|---|---|---|
| | BR10 | BR11 |
| 1 | DR11 | DR12 |
| 2 | DR12 | DR12 |

FIG. 20

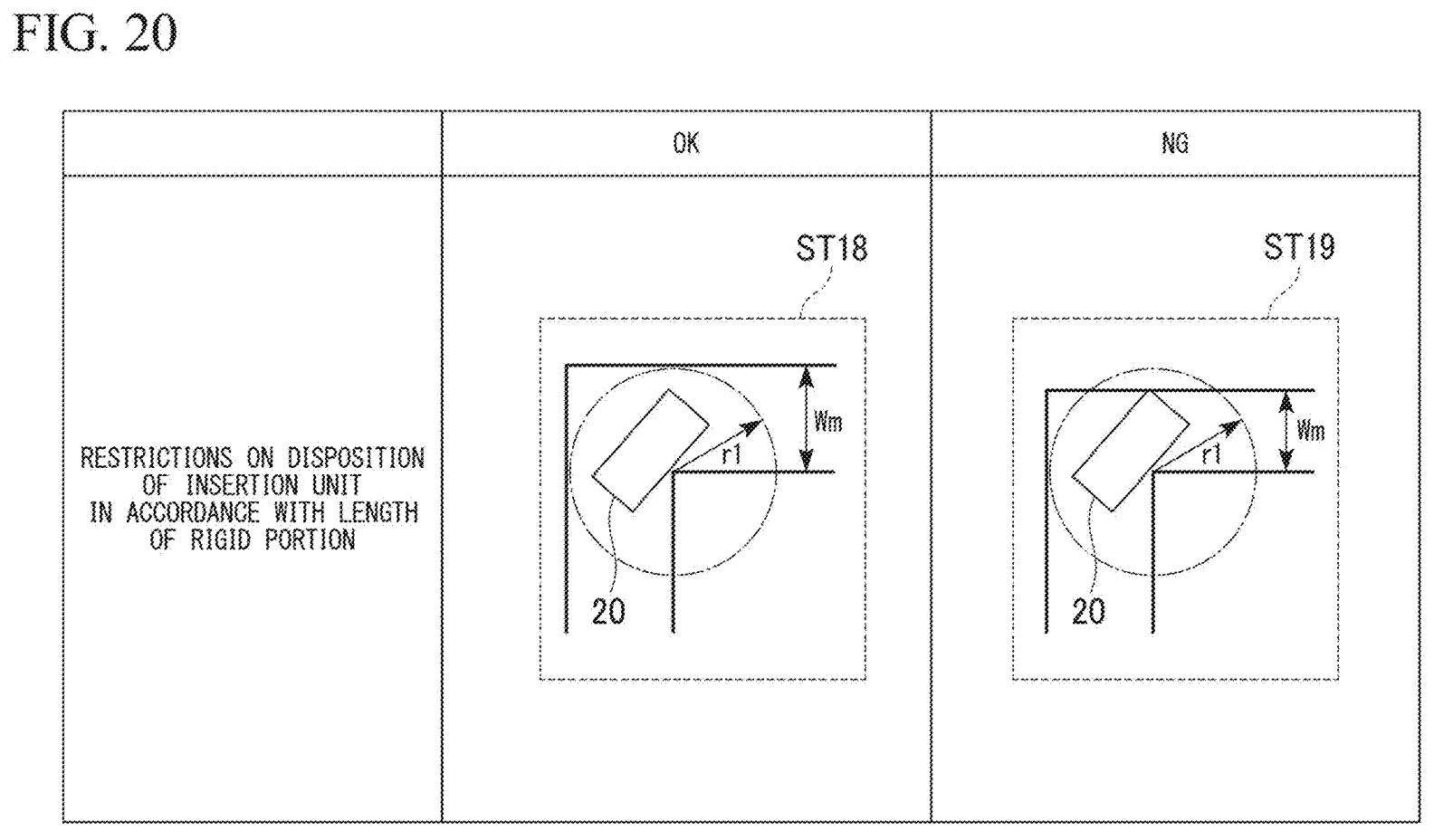

RESTRICTIONS ON DISPOSITION OF INSERTION UNIT IN ACCORDANCE WITH LENGTH OF RIGID PORTION

| PATH CANDIDATE | ANALYSIS RESULT | | | |
|---|---|---|---|---|
| | BENDING LOAD | CHARACTERISTICS OF SLOPE | RESTRICTIONS ON DISPOSITION | PATH LENGTH |
| 1 | C | B | A | 1.0m |
| 2 | B | A | C | 1.3m |
| 3 | A | C | A | 1.7m |
| 4 | B | A | A | 2.0m |
| : | : | : | : | : |

INSERTION ASSISTANCE SYSTEM, INSERTION ASSISTANCE METHOD, AND RECORDING MEDIUM

BACKGROUND OF THE INVENTION

Field of the Invention

The present invention relates to an insertion assistance system, an insertion assistance method, and a recording medium.

Priority is claimed on Japanese Patent Application No. 2021-123407, filed on Jul. 28, 2021, the content of which is incorporated herein by reference.

Description of Related Art

Industrial endoscope devices have been used for inspection of internal abnormalities, corrosion, and the like of boilers, pipes, aircraft engines, and the like. An endoscope device includes an insertion unit used for acquiring an image. A user inserts the insertion unit into a subject and acquires an image of an inspection portion in the subject. The user observes the image and inspects the inspection portion.

In medical fields, a technique for calculating a path for inserting an endoscope by using three-dimensional (3D) image data of a living body is used. The technique acquires the 3D image data by using a method such as CT scanning in which a living body is irradiated with X-rays. The technique can determine the most appropriate path for inserting the endoscope such that walls of a narrow organ such as a lung are not damaged in an inspection of the organ.

A technique disclosed in Japanese Patent No. 6030435 provides a method of determining a direction of a distal end of an endoscope on the basis of inner diameters of bronchi. A technique disclosed in Japanese Patent No. 5123615 provides a method of selecting a path on the basis of the smallest curvature of paths.

In the field of industrial endoscope devices, a similar technique to that described above is used. A technique disclosed in Japanese Patent No. 4464640 sets a path for inserting an endoscope by using 3D shape information of a subject. If an insertion unit passes between protrusions or passes through very narrow places or places in which the insertion unit needs to be greatly bent, it is confirmed that the path is inappropriate. In this case, another path is suggested.

Since the path calculation function described above is provided, efficiency of work in which an inspector inserts an insertion unit at an inspection site is improved. In addition, the inspector can easily cause the insertion unit to reach an inspection portion regardless of inspection skills of the inspector and can perform a highly reliable inspection.

SUMMARY OF THE INVENTION

According to a first aspect of the present invention, an insertion assistance system is configured to assist an insertion operation of an insertion unit when the insertion unit is inserted into a subject. The insertion unit includes a lens that is disposed at a distal end of the insertion unit and is configured to acquire an optical image of the subject. The insertion assistance system includes a processor. The processor is configured to set a first position and a second position in shape information indicating a three-dimensional shape of the subject. The first position indicates a target position. The second position is different from the first position. The processor is configured to estimate a first state of the distal end at the first position on the basis of a specification of the insertion unit. The processor is configured to calculate a path through which the distal end passes when the distal end moves from the second position to the first position. The processor is configured to determine a second state of the distal end at the second position. The processor is configured to output, to an information-reporting device, insertion assistance information required for the insertion operation for causing the distal end to reach the first position from the second position through the path and causing a state of the distal end to change from the second state to the first state.

According to a second aspect of the present invention, in the first aspect, in a case in which the three-dimensional shape includes a branch portion, the processor may be configured to record the branch portion through which the distal end disposed at the first position in the first state passes while the distal end moves from the first position to the second position in the three-dimensional shape. The processor may be configured to calculate two or more path candidates including a path candidate passing through the branch portion. The processor may be configured to select one of the two or more path candidates as the path.

According to a third aspect of the present invention, in the first aspect, in a case in which the three-dimensional shape includes a branch portion, the processor may be configured to calculate two or more path candidates including a path candidate passing through the branch portion. The processor may be configured to analyze the two or more path candidates in accordance with one or more indices related to at least one of the insertion unit and the subject. The processor may be configured to select one of the two or more path candidates as the path on the basis of a result of analyzing the two or more path candidates.

According to a fourth aspect of the present invention, in the third aspect, a degree of importance may be set for each of two or more indices including the one or more indices in advance. The processor may be configured to analyze the two or more path candidates in accordance with the two or more indices and the degree of importance.

The degree of importance set for each of the two or more indices may be variable.

According to a fifth aspect of the present invention, in the third aspect, the processor may be configured to analyze the two or more path candidates by using at least one of information indicating a size of the insertion unit and information indicating a shape of the subject.

According to a sixth aspect of the present invention, in the first aspect, when the insertion operation is performed, the processor may be configured to determine a position of the distal end and set the second position to the determined position.

According to a seventh aspect of the present invention, in the first aspect, the processor may be configured to estimate the first state causing a state of the distal end at the first position to be at least one of a first observation state, a second observation state, and a third observation state. The first observation state is a state in which a direction of an optical axis of the lens is perpendicular to a surface of the subject. The second observation state is a state in which a predetermined direction in the distal end matches a predetermined direction in the three-dimensional shape. The third observation state is a state in which a distance between the distal end and the subject is appropriate for observation of the subject.

According to an eighth aspect of the present invention, in the first aspect, the insertion operation may indicate at least one of an operation of moving the insertion unit in the subject, an operation of bending the insertion unit, and an operation of twisting the insertion unit.

According to a ninth aspect of the present invention, in the first aspect, the insertion assistance information may include at least one of a distance between the second position and the first position, an amount of change of a direction of the distal end to cause the direction of the distal end to match a direction along the path, and an amount of twist to cause a twist state of the insertion unit to match a twist state of the insertion unit in the first state.

According to a tenth aspect of the present invention, in the first aspect, the insertion assistance information may include a history of a position through which the distal end passes.

According to an eleventh aspect of the present invention, in the first aspect, the processor may be configured to calculate the path on the basis of a specification of an optical adaptor mounted on the distal end.

According to a twelfth aspect of the present invention, an insertion assistance method assists an insertion operation of an insertion unit when the insertion unit is inserted into a subject. The insertion unit includes a lens that is disposed at a distal end of the insertion unit and is configured to acquire an optical image of the subject. The insertion assistance method includes a setting step, a state estimation step, a path calculation step, a state determination step, and an insertion assistance step. A processor sets a first position and a second position in shape information indicating a three-dimensional shape of the subject in the setting step. The first position indicates a target position. The second position is different from the first position. The processor estimates a first state of the distal end at the first position on the basis of a specification of the insertion unit in the state estimation step. The processor calculates a path through which the distal end passes when the distal end moves from the second position to the first position in the path calculation step. The processor determines a second state of the distal end at the second position in the state determination step. The processor outputs, to an information-reporting device, insertion assistance information required for the insertion operation for causing the distal end to reach the first position from the second position through the path and causing a state of the distal end to change from the second state to the first state in the insertion assistance step.

According to a thirteenth aspect of the present invention, a non-transitory computer-readable recording medium stores a program causing a computer to execute processing of assisting an insertion operation of an insertion unit when the insertion unit is inserted into a subject. The insertion unit includes a lens that is disposed at a distal end of the insertion unit and is configured to acquire an optical image of the subject. The processing includes a setting step, a state estimation step, a path calculation step, a state determination step, and an insertion assistance step. The computer sets a first position and a second position in shape information indicating a three-dimensional shape of the subject in the setting step. The first position indicates a target position. The second position is different from the first position. The computer estimates a first state of the distal end at the first position on the basis of a specification of the insertion unit in the state estimation step. The computer calculates a path through which the distal end passes when the distal end moves from the second position to the first position in the path calculation step. The computer determines a second state of the distal end at the second position in the state determination step. The computer outputs, to an information-reporting device, insertion assistance information required for the insertion operation for causing the distal end to reach the first position from the second position through the path and causing a state of the distal end to change from the second state to the first state in the insertion assistance step.

BRIEF DESCRIPTION OF THE DRAWINGS

FIG. 11 is a diagram showing an example of a target state of the distal end portion of the insertion unit in the embodiment of the present invention.

FIG. 15A is a diagram showing an example of a branch management table in the embodiment of the present invention.

FIG. 15B is a diagram showing an example of a branch management table in the embodiment of the present invention.

FIG. 15C is a diagram showing an example of a branch management table in the embodiment of the present invention.

FIG. 15D is a diagram showing an example of a branch management table in the embodiment of the present invention.

FIG. 20 is a diagram showing an example of restrictions on the disposition of the insertion unit in accordance with the length of a rigid portion of the insertion unit in the embodiment of the present invention.

FIG. 21 is a diagram showing an example of restrictions on the disposition of the insertion unit in accordance with a bending length of the insertion unit in the embodiment of the present invention.

DETAILED DESCRIPTION OF THE INVENTION

Figure 1:
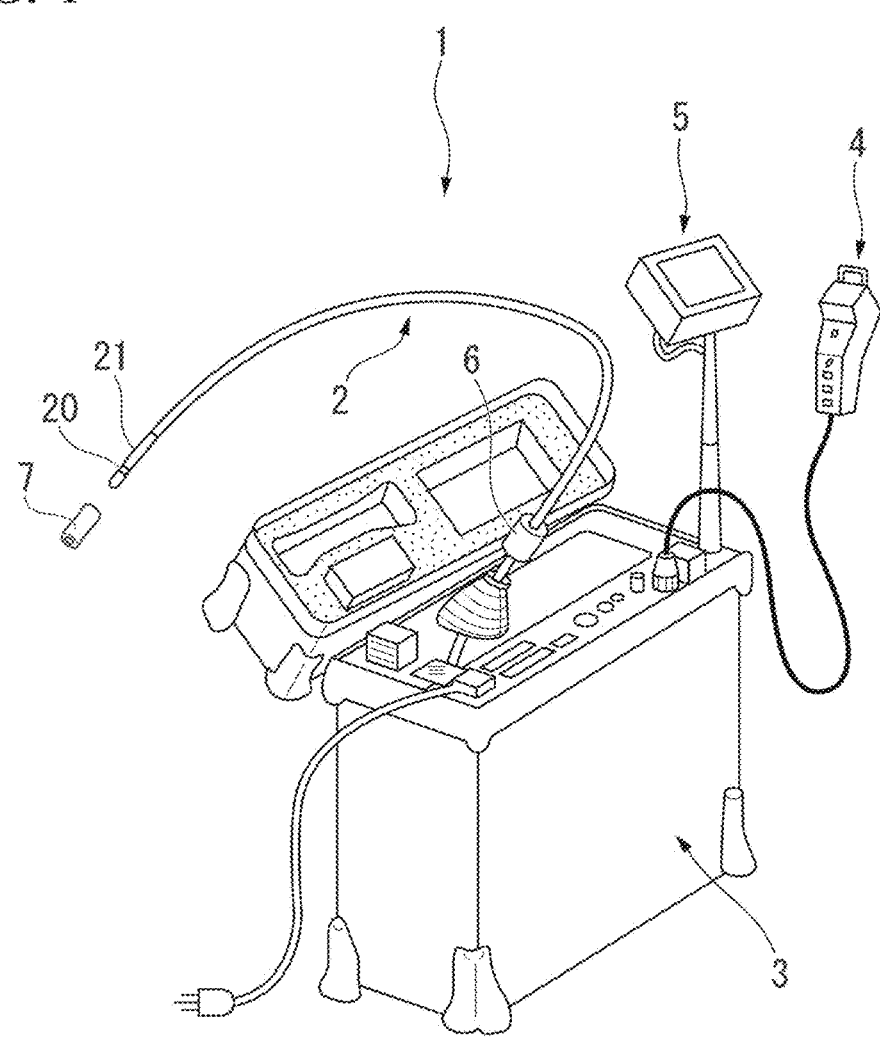
FIG. 1 is a perspective view showing an entire configuration of an endoscope device according to an embodiment of the present invention.

Hereinafter, embodiments of the present invention will be described with reference to the drawings. FIG. 1 shows an external appearance of an endoscope device 1 (insertion assistance system) according to an embodiment of the present invention. The endoscope device 1 shown in FIG. 1 includes an insertion unit 2, a main body unit 3, an operation unit 4, a display unit 5, and an insertion-length determination unit 6.

The insertion unit 2 is inserted into the inside of a subject. A user (inspector) performs an insertion operation and inserts the insertion unit 2 into the subject. The insertion unit 2 has a long and thin bendable tube shape. The insertion unit 2 includes a distal end portion 20 and a bending portion 21. The distal end portion 20 is disposed in the distal end of the insertion unit 2. The distal end portion 20 includes a rigid portion formed of a rigid material. An optical adaptor 7 is mounted on the distal end portion 20. The bending portion 21 is disposed on the base end side of the distal end portion 20. The bending portion 21 is capable of bending in a predetermined direction. The insertion unit 2 converts an optical image of the subject into an imaging signal and outputs the imaging signal to the main body unit 3.

The main body unit 3 is a control device including a housing unit that houses the insertion unit 2. The operation unit 4 accepts an operation for the endoscope device 1 from a user. The display unit 5 includes a display screen and displays an image of a subject acquired by the insertion unit 2 on the display screen.

The operation unit 4 is a user interface (input device). For example, the operation unit 4 is at least one of a button, a switch, a key, a mouse, a joystick, a touch pad, a track ball, and a touch panel. A user bends the bending portion 21 by performing a bending operation using the operation unit 4. Alternatively, the user controls the state of illumination by operating the operation unit 4. In addition, the user inputs information used for setting the state of the endoscope device 1 into the endoscope device 1 by operating the operation unit 4. An input device including the operation unit 4 may be connected to the main body unit 3 by using wired or wireless connection.

The display unit 5 is a monitor (display) such as a liquid crystal display (LCD). The display unit 5 may be a touch panel. In such a case, the operation unit 4 and the display unit 5 are integrated. A user touches the screen of the display unit 5 by using a part of the body or a tool. For example, the part of the body is the finger. The display unit 5 may be connected to the main body unit 3 by using wired or wireless connection. In a case in which the operation unit 4 and the display unit 5 are integrated, an information terminal such as a tablet, a smartphone, or a personal computer may be used as a terminal including the display unit 5.

For example, the insertion-length determination unit 6 includes a rotary encoder and two rollers. The two rollers are disposed so as to locate the insertion unit 2 therebetween. The two rollers are in contact with the insertion unit 2. The two rollers rotate as the insertion unit 2 moves. The rotary encoder determines the amount of rotation of at least one of the two rollers, thus determining the length (insertion length) of the insertion unit 2 inserted into a space in a subject. The length corresponds to the position of the distal end portion 20.

A user performs the bending operation and the insertion operation while viewing an image displayed on the display unit 5. When the insertion unit 2 is inserted into a subject, the endoscope device 1 assists the insertion operation of the insertion unit 2. The user searches for an inspection portion and disposes the distal end portion 20 so that the inspection portion can be seen in an image in an appropriate state. Thereafter, the user performs an inspection of the subject.

Figure 2:
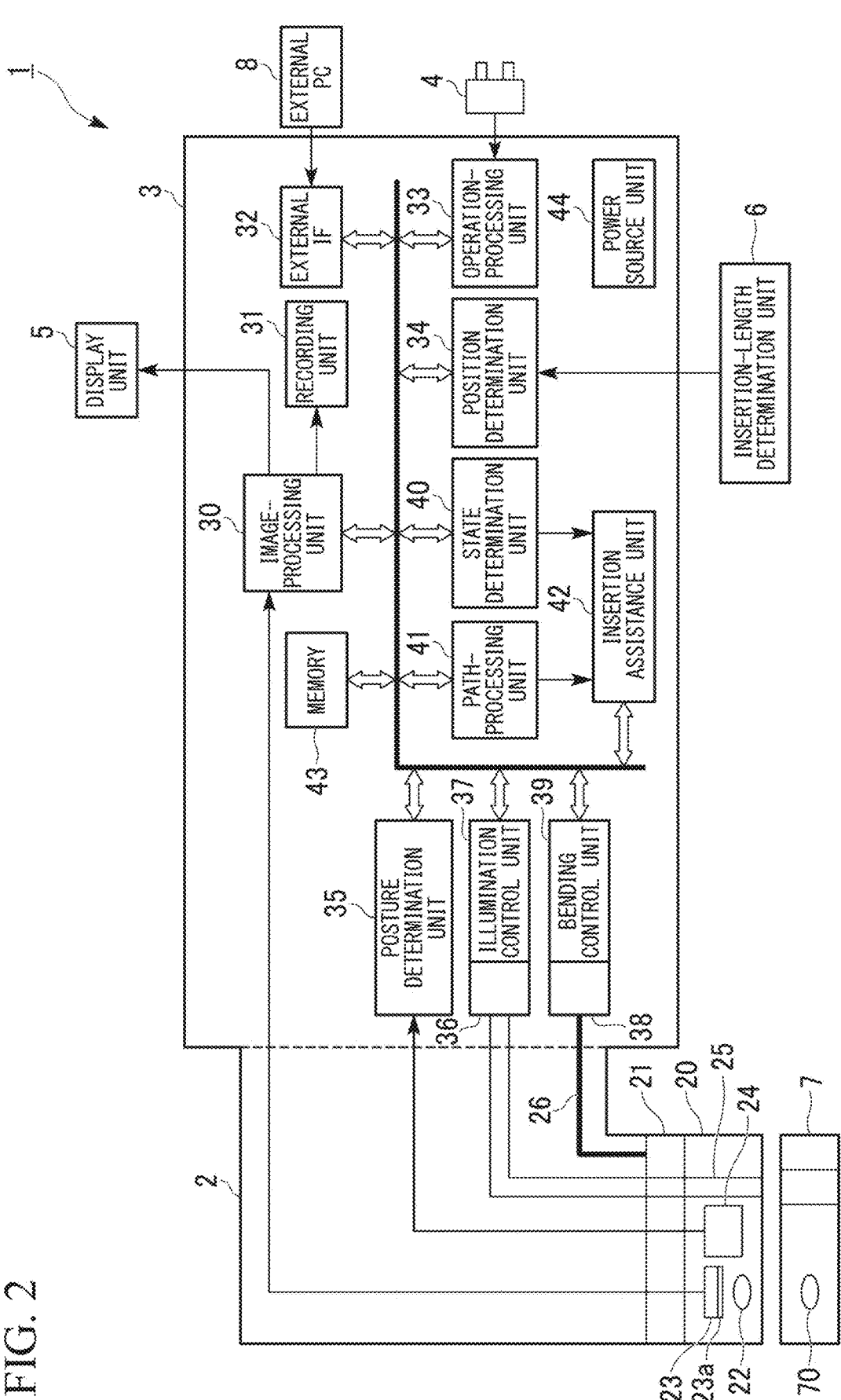
FIG. 2 is a block diagram showing an internal configuration of the endoscope device according to the embodiment of the present invention.

FIG. 2 shows an internal configuration of the endoscope device 1. The distal end portion 20 of the insertion unit 2 includes a lens 22, an imaging device 23, and a posture sensor 24.

The main body unit 3 includes an image-processing unit 30, a recording unit 31, an external interface (IF) 32, an operation-processing unit 33, a position determination unit 34, a posture determination unit 35, a light source 36, an illumination control unit 37, a motor 38, a bending control unit 39, a state determination unit 40, a path-processing unit 41, an insertion assistance unit 42, a memory 43, and a power source unit 44.

The optical adaptor 7 includes a lens 70. Light incident on the lens 70 passes through the lens 70 and is incident on the lens 22. The lens 70 and the lens 22 constitute an observation optical system. The light incident on the lens 22 passes through the lens 22 and is incident on the imaging device 23. The imaging device 23 is an image sensor such as a CCD sensor or a CMOS sensor. The imaging device 23 includes an imaging surface 23a on which the light passing through the lens 22 is incident. The imaging device 23 converts the light incident on the imaging surface 23a into an imaging signal.

The imaging signal generated by the imaging device 23 includes an image of a subject. Accordingly, the imaging device 23 acquires an optical image of the subject and generates an image of the subject. The image generated by the imaging device 23 is output to the main body unit 3.

The posture sensor 24 includes at least one of an acceleration sensor of three axes, a gyro sensor of three axes, and a geomagnetic sensor. The posture sensor 24 measures a value related to the posture of the distal end portion 20 and outputs the measured value to the main body unit 3. The value indicates at least one of an acceleration, an angular velocity, and a geomagnetic field.

The image-processing unit 30 processes the imaging signal output from the imaging device 23, thus processing an image of a subject. For example, the image-processing unit 30 executes processing such as noise elimination, brightness adjustment, and color adjustment in order to enhance the quality of the image. In addition, the image-processing unit 30 executes localization such as visual simultaneous localization and mapping (Visual SLAM) and calculates a position and a posture of the distal end portion 20. Furthermore, the image-processing unit 30 superimposes insertion assistance information generated by the insertion assistance unit 42 on the image of the subject.

The image processed by the image-processing unit 30 is output to the display unit 5 or the recording unit 31. The display unit 5 displays the image processed by the image-processing unit 30. The recording unit 31 includes a recording medium and records the image processed by the image-processing unit 30 on the recording medium.

The external IF 32 is connected to an external PC 8. The external PC 8 is a versatile personal computer. The external PC 8 outputs subject information. An information terminal such as a tablet or a smartphone may be used instead of the external PC.

The subject information includes shape information, material information, and position information. The shape information indicates a 3D shape (3D model) of a subject. For example, the shape information is generated by using 3D-CAD.

Alternatively, the shape information is generated from an image acquired in a previous inspection by using a technique such as SLAM. The shape information includes 3D coordinates of three or more points of the subject. The shape information generated by using a technique such as SLAM includes the 3D coordinates and includes position information and posture information of a camera that acquires the image. The material information indicates the material of the subject. The position information indicates at least one of an origin and a destination in the 3D shape. The origin indicates a position at which the distal end portion 20 is disposed when the insertion operation is performed. The destination indicates a target position, which is an observation position of the subject. For example, the 3D shape indicated by the shape information is displayed on the display unit 5. A user designates the origin and the destination in the 3D shape in advance by operating the operation unit 4.

The subject information output from the external PC 8 is input into the external IF 32. The external IF 32 outputs the subject information to the path-processing unit 41.

The external IF 32 may be connected to a server on a network (cloud). The subject information may be output from the server and may be input into the external IF 32.

The external IF 32 may be connected to a recording medium such as a memory card that stores the subject information. The subject information may be read from the recording medium and may be input into the external IF 32.

The operation-processing unit 33 is connected to the operation unit 4. The operation unit 4 outputs information in accordance with an operation performed by a user. The operation-processing unit 33 sets the state of the endoscope device 1 to be a state in accordance with the information output from the operation unit 4.

The position determination unit 34 determines a position of the distal end portion 20 inside a subject on the basis of the insertion length output from the insertion-length determination unit 6. The posture determination unit 35 determines a posture of the distal end portion 20 on the basis of the value output from the posture sensor 24.

The light source 36 is a light-emitting diode (LED) or the like and generates illumination light. The illumination light is emitted from the distal end portion 20 via a light guide 25 disposed in the insertion unit 2. The illumination control unit 37 controls the light source 36 on the basis of the information output from the operation unit 4, thus setting turning-on and turning-off of illumination and the intensity of the illumination.

The motor 38 is connected to a plurality of angle wires 26. The plurality of angle wires 26 are disposed in the insertion unit 2 and are connected to the bending portion 21. The motor 38 pulls the plurality of angle wires 26, thus bending the bending portion 21. The bending control unit 39 controls the motor 38 on the basis of the information output from the operation unit 4, thus controlling the angle of the bending portion 21. In other words, the bending control unit 39 controls the posture of the distal end portion 20.

The state determination unit 40 determines the position and the posture of the distal end portion 20. The state determination unit 40 outputs information indicating the determined position and posture to the insertion assistance unit 42. The path-processing unit 41 calculates an optimal path through which the distal end portion 20 passes until the distal end portion 20 reaches the target position. The insertion assistance unit 42 generates insertion assistance information used for assisting the insertion operation of the insertion unit 2.

The memory 43 stores information processed by the endoscope device 1. The memory 43 is, for example, a semiconductor memory and may include a RAM region and a ROM region. The power source unit 44 supplies each unit of the endoscope device 1 with driving power.

At least one of the image-processing unit 30, the operation-processing unit 33, the position determination unit 34, the posture determination unit 35, the illumination control unit 37, the bending control unit 39, the state determination unit 40, the path-processing unit 41, and the insertion assistance unit 42 may be constituted by at least one of a processor and a logic circuit. For example, the processor is at least one of a central processing unit (CPU), a digital signal processor (DSP), and a graphics-processing unit (GPU). For example, the logic circuit is at least one of an application-specific integrated circuit (ASIC) and a field-programmable gate array (FPGA). The image-processing unit 30 and the like may include one or a plurality of processors. The image-processing unit 30 and the like may include one or a plurality of logic circuits.

A computer of the endoscope device 1 may read a program and execute the read program. The program includes commands defining the operations of the image-processing unit 30 and the like. In other words, the functions of the image-processing unit 30 and the like may be realized by software.

The program described above, for example, may be provided by using a "computer-readable storage medium" such as a flash memory. The program may be transmitted from the computer storing the program to the endoscope device 1 through a transmission medium or transmission waves in a transmission medium. The "transmission medium" transmitting the program is a medium having a function of transmitting information. The medium having the function of transmitting information includes a network (communication network) such as the Internet and a communication circuit line (communication line) such as a telephone line. The program described above may realize some of the functions described above. In addition, the program described above may be a differential file (differential program). The functions described above may be realized by a combination of a program that has already been recorded in a computer and a differential program.

Figure 3:
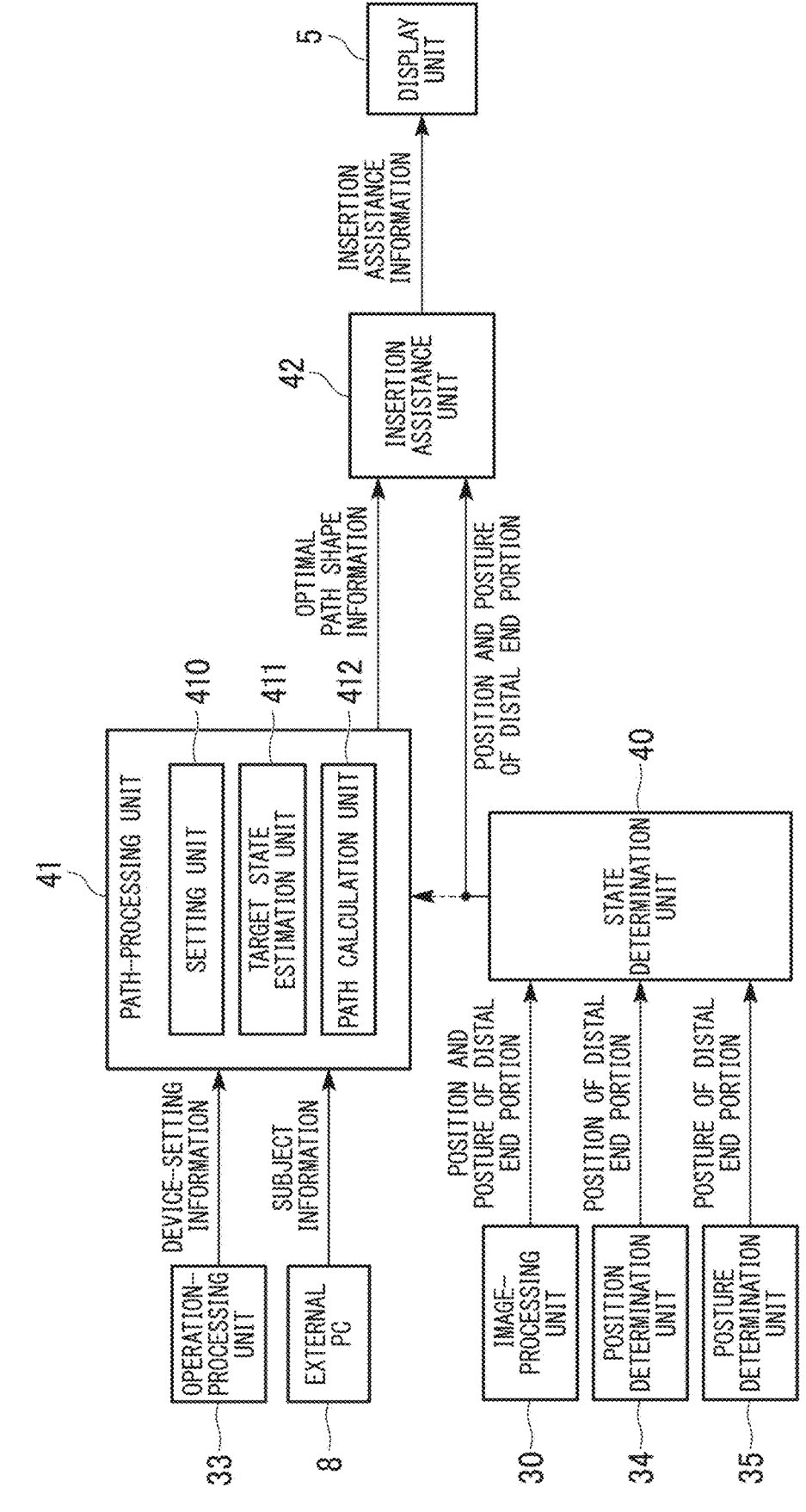
FIG. 3 is a block diagram showing a main configuration of the endoscope device according to the embodiment of the present invention.

FIG. 3 shows a main configuration of the endoscope device 1. Processing for assisting the insertion operation of the insertion unit 2 will be described by using FIG. 3.

An outline of the configuration shown in FIG. 3 will be described. The path-processing unit 41 includes a setting unit 410, a target state estimation unit 411 (state estimation unit), and a path calculation unit 412. The setting unit 410 sets the destination (first position) and the origin (second position) in the shape information. The shape information indicates a 3D shape of a subject. The destination indicates a target position. The origin is different from the destination. The target state estimation unit 411 estimates a first state of the distal end portion 20 at the destination on the basis of a specification of the insertion unit 2. The path calculation unit 412 calculates a path through which the distal end portion 20 passes when the distal end portion 20 moves from the origin to the destination. The state determination unit 40 determines a second state of the distal end portion 20 at the origin. The insertion assistance unit 42 outputs, to the display unit 5 (information-reporting device), insertion assistance information required for the insertion operation for causing the distal end portion 20 to reach the destination from the origin through the above-described path and causing a state of the distal end portion 20 to change from the second state to the first state.

Details of the configuration shown in FIG. 3 will be described. The operation-processing unit 33 acquires device-setting information on the basis of the information output from the operation unit 4. The device-setting information includes insertion unit information and optical adaptor information. The insertion unit information indicates a specification of the insertion unit 2. The optical adaptor information indicates a specification of the optical adaptor 7.

The image-processing unit 30 may have an image rotation function. In a case in which the image-processing unit 30 has the image rotation function, the image-processing unit 30 can rotate an image in any direction. The device-setting information may include information indicating whether the image rotation function is set.

As a type of the optical adaptor 7, which is one of the specifications of the optical adaptor 7, there are a direct-view adaptor and a side-view adaptor. The direct-view adaptor acquires an optical image of a subject seen in the longitudinal direction of the insertion unit 2. The side-view adaptor acquires an optical image of the subject seen in a perpendicular direction to the side of the insertion unit 2. There is an optical adaptor capable of switching between a direct-view state and a side-view state. The device-setting information may include information indicating any one of the direct-view state and the side-view state.

For example, the memory 43 stores the device-setting information. A user inputs information of the insertion unit 2 and the optical adaptor 7 to be used into the endoscope device 1 by operating the operation unit 4. The operation-processing unit 33 identifies the insertion unit 2 and the optical adaptor 7 to be used on the basis of the information output from the operation unit 4. The operation-processing unit 33 acquires the insertion unit information corresponding to the identified insertion unit 2 from the memory 43 and acquires the optical adaptor information corresponding to the identified optical adaptor 7 from the memory 43.

As described above, the external PC 8 outputs the subject information. The subject information includes the shape information, the material information, and the position information described above. The external PC 8 may output the device-setting information. The device-setting information output from the external PC 8 may be input into the external IF 32.

The image-processing unit 30 executes the localization such as SLAM and calculates the position and the posture of the distal end portion 20. The image-processing unit 30 outputs information indicating each of the calculated position and posture. The position determination unit 34 determines the position of the distal end portion 20 and outputs information indicating the determined position. The posture determination unit 35 determines the posture of the distal end portion 20 and outputs information indicating the determined posture.

The state determination unit 40 determines the position and the posture of the distal end portion 20 on the basis of the information output from the image-processing unit 30, the position determination unit 34, and the posture determination unit 35. The state determination unit 40 does not need to use all the above-described information. The state determination unit 40 may determine the position of the distal end portion 20 by using one or both of the position calculated by the image-processing unit 30 and the position determined by the position determination unit 34. The state determination unit 40 may determine the posture of the distal end portion 20 by using one or both of the posture calculated by the image-processing unit 30 and the posture determined by the posture determination unit 35. The state determination unit 40 may select information used for determining the position or the posture of the distal end portion 20 in accordance with the structure of the subject or required positional accuracy.

The state determination unit 40 may determine a bending state of the bending portion 21 on the basis of the information output from the bending control unit 39. In this way, the state determination unit 40 can determine a schematic shape of the bending portion 21. The state determination unit 40 may use the schematic shape of the bending portion 21 in addition to the posture determined by the image-processing unit 30 or the posture determination unit 35 in order to determine the posture of the distal end portion 20.

The setting unit 410 sets the destination and the origin on the basis of the position information included in the subject information. The setting unit 410 may set the present position of the distal end portion 20 as the origin. In such a case, the setting unit 410 sets the position of the distal end portion 20 output from the state determination unit 40 as the origin.

The target state estimation unit 411 estimates a target state of the distal end portion 20 in a state in which the distal end portion 20 is hypothetically disposed at the destination. The target state indicates an appropriate state for observation of the subject. The setting unit 410 sets a position at which the target state is realized as the destination.

The path calculation unit 412 hypothetically moves the distal end portion 20 on the 3D shape of the subject from the destination toward the origin and records a path through which the distal end portion 20 passes. In a case in which the 3D shape does not include a branch portion, the path calculation unit 412 calculates one or more path candidates. In a case in which the 3D shape includes one or more branch portions, the path calculation unit 412 considers a branch pattern at each branch portion and calculates two or more path candidates. The path calculation unit 412 analyzes the state of the insertion unit 2 when the insertion unit 2 passes through each path candidate and selects any one of the one or more path candidates as an optimal path.

The insertion assistance unit 42 generates insertion assistance information on the basis of the position and the posture of the distal end portion 20 determined by the state determination unit 40, the optimal path calculated by the path-processing unit 41, and the shape information included in the subject information. Specifically, the insertion assistance unit 42 calculates the amount of shift between an ideal posture of the distal end portion 20 in the optimal path and the present posture of the distal end portion 20. At this time, the insertion assistance unit 42 calculates the amount of shift between a twist state of the insertion unit 2 in the optimal path and the present twist state of the insertion unit 2. The twist state of the insertion unit 2 indicates a rotational position of the insertion unit 2 around a center axis of the insertion unit 2 extending in the longitudinal direction of the insertion unit 2.

The insertion assistance unit 42 generates insertion assistance information. The insertion assistance information includes information used for assisting an operation for adjusting the posture of the distal end portion 20. In addition, the insertion assistance information includes information used for assisting an operation for adjusting the twist state of the insertion unit 2. The insertion assistance unit 42 outputs the insertion assistance information to the display unit 5 via the image-processing unit 30.

Figure 4:
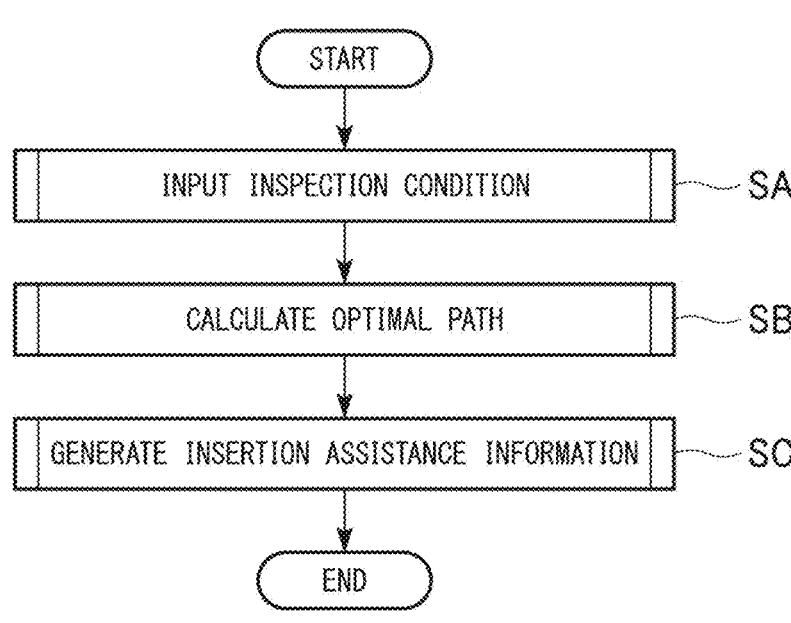
FIG. 4 is a flow chart showing a procedure of an operation of the endoscope device according to the embodiment of the present invention.

FIG. 4 shows main processing executed by the endoscope device 1. An inspection condition including the subject information and the device-setting information is input into the endoscope device 1 (Step SA). After Step SA, the path-processing unit 41 calculates an optimal path (Step SB). After Step SB, the insertion assistance unit 42 generates insertion assistance information (Step SC). When Step SC is executed, the processing shown in FIG. 4 is completed. The processing shown in FIG. 4 may be repeated.

Figure 5:
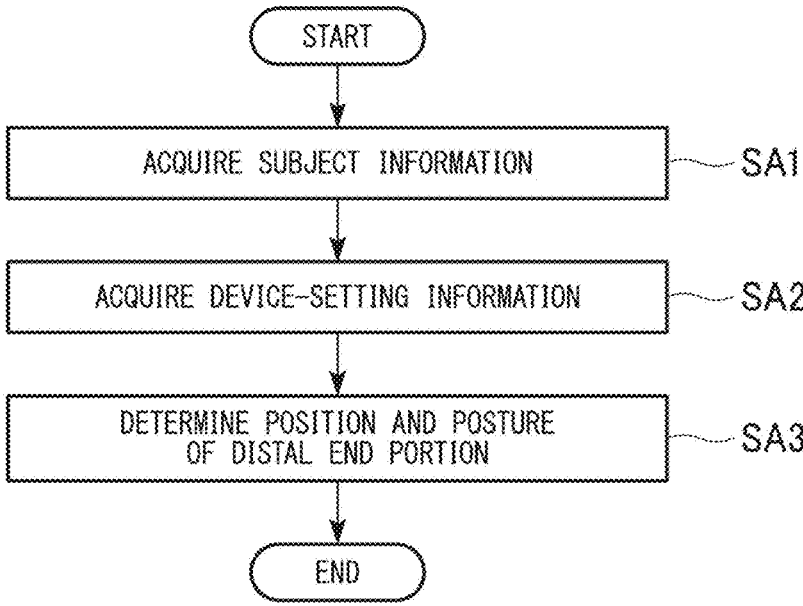
FIG. 5 is a flow chart showing a procedure of an operation of the endoscope device according to the embodiment of the present invention.

FIG. 5 shows processing executed in Step SA shown in FIG. 4. The external IF 32 acquires the subject information output from the external PC 8 (Step SA1). After Step SAL, the operation-processing unit 33 acquires the device-setting information on the basis of the information output from the operation unit 4 (Step SA2). After Step SA2, the state determination unit 40 determines the position and the posture of the distal end portion 20 (Step SA3). When Step SA3 is executed, the processing shown in FIG. 5 is completed.

The order of Step SA1, Step SA2, and Step SA3 is not limited to that shown in FIG. 5. Step SA1, Step SA2, and Step SA3 may be executed in any order.

Figure 6:
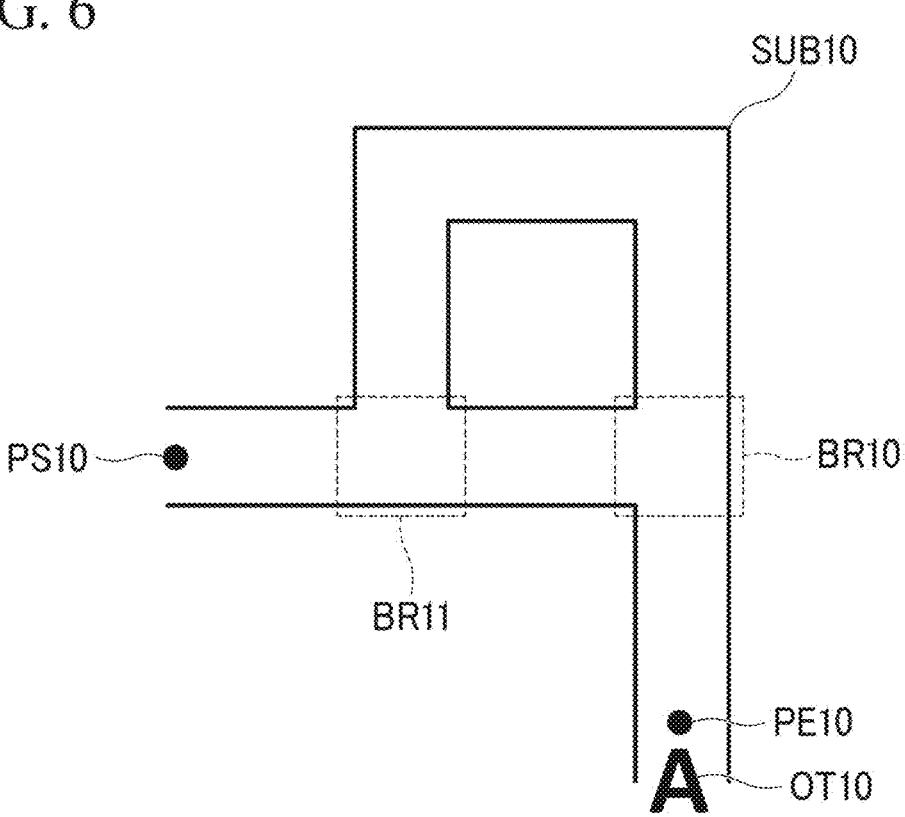
FIG. 6 is a diagram showing an example of shape information and position information in the embodiment of the present invention.

FIG. 6 shows an example of the shape information and the position information included in the subject information. The shape information indicates a 3D shape SUB10 of a subject. The subject shown in FIG. 6 is a pipe. The position information indicates an origin PS10 and a destination PE10. The 3D shape SUB10 includes a branch portion BR10 and a branch portion BR11. A path heading from the origin PS10 toward the destination PE10 branches into two paths at the branch portion BR11. The two paths join at the branch portion BR10.

The position of an observation target OT10 shown in FIG. 6 and the direction of the observation target OT10 are set in advance. The observation target OT10 is an inspection portion. The subject information also includes information of these.

Figure 7:
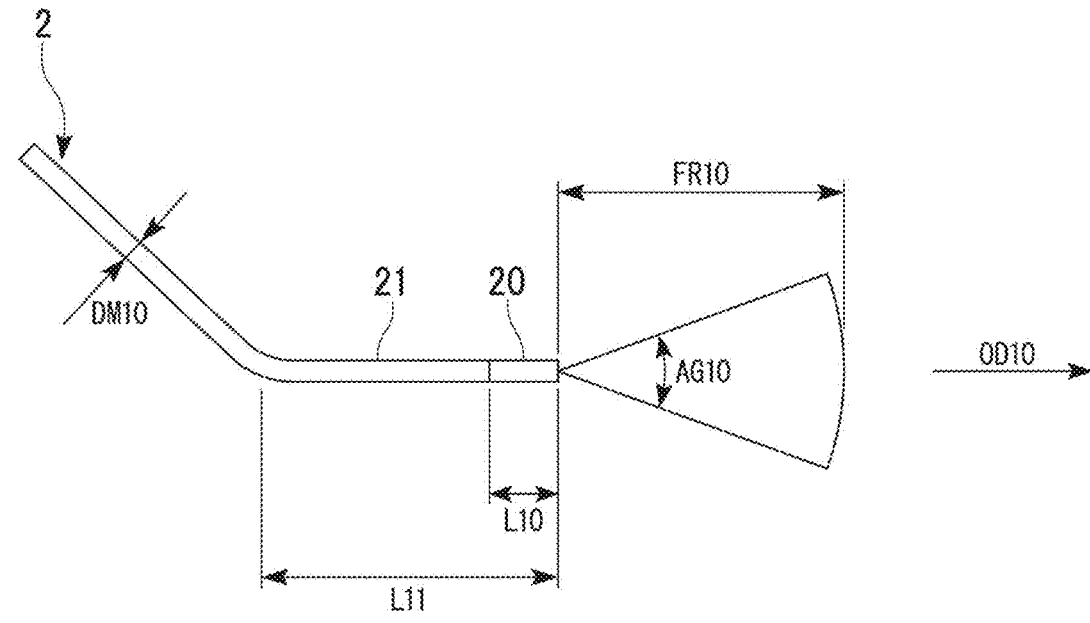
FIG. 7 is a diagram showing an example of device-setting information in the embodiment of the present invention.

FIG. 7 shows an example of the device-setting information. The device-setting information includes insertion unit information including a specification of the insertion unit 2 and optical adaptor information including a specification of the optical adaptor 7. The insertion unit information includes information indicating a diameter DM10 of the insertion unit 2. The insertion unit information includes information indicating each of a rigid portion length L10 and a bending length L11. The rigid portion length L10 indicates the length of the rigid portion of the distal end portion 20. The bending length L11 indicates the total length of the distal end portion 20 and the bending portion 21. The optical adaptor information includes information indicating an observation direction OD10 of the optical adaptor 7. The observation direction OD10 is parallel to an optical axis of an observation optical system such as the lens 70. The optical adaptor information includes information indicating each of a focal range FR10 of the optical adaptor 7 and a field angle AG10 of the optical adaptor 7.

Figure 8:
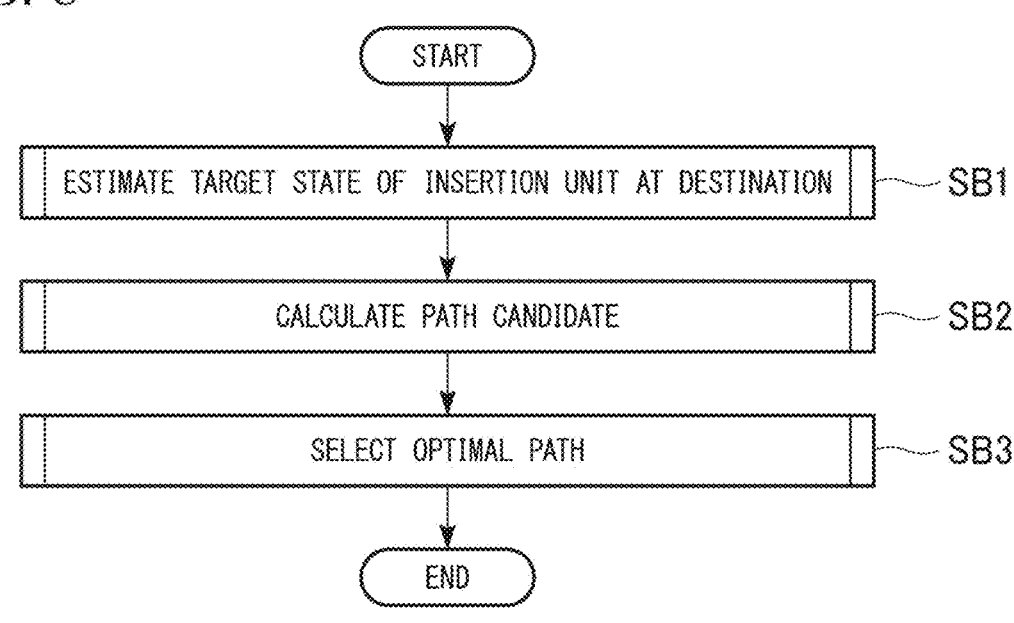
FIG. 8 is a flow chart showing a procedure of an operation of the endoscope device according to the embodiment of the present invention.

FIG. 8 shows processing executed in Step SB shown in FIG. 4. The target state estimation unit 411 estimates a target state of the distal end portion 20 at the destination (Step SB1). After Step SB1, the path calculation unit 412 calculates one or more path candidates in which the state of the distal end portion 20 at the destination becomes the target state (Step SB2). After Step SB2, the path calculation unit 412 selects any one of the one or more path candidates as an optimal path (Step SB3). When Step SB3 is executed, the processing shown in FIG. 8 is completed.

Figure 9:
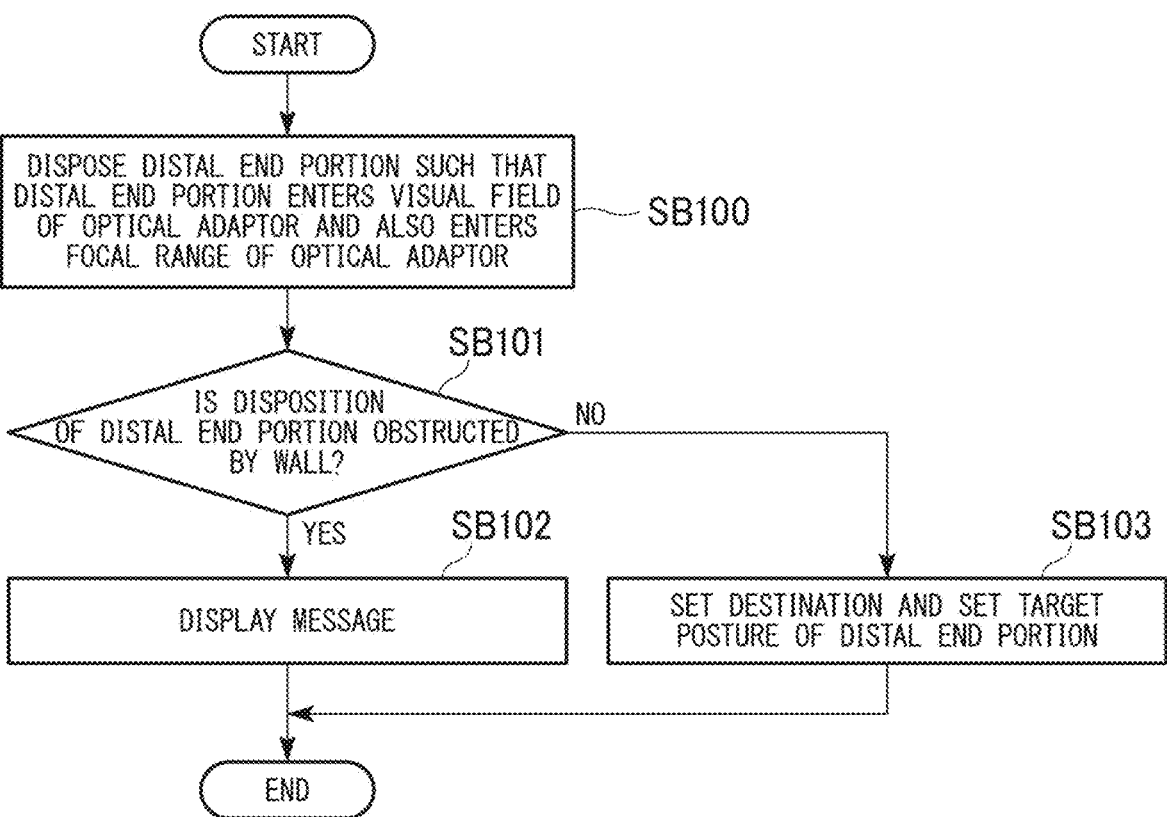
FIG. 9 is a flow chart showing a procedure of an operation of the endoscope device according to the embodiment of the present invention.

FIG. 9 shows processing executed in Step SB1 shown in FIG. 8. It is assumed that the insertion unit 2 is inserted into a subject and reaches an inspection portion. The position and the posture of the distal end portion 20 in this state are estimated. In the following processing, the distal end portion 20 is hypothetically disposed on the 3D shape indicated by the shape information included in the subject information.

To begin with, the target state estimation unit 411 refers to the position information included in the subject information acquired in Step SA1 and disposes the distal end portion 20 at the destination indicated by the position information. At this time, the target state estimation unit 411 refers to the optical adaptor information included in the device-setting information acquired in Step SA2. The target state estimation unit 411 disposes the distal end portion 20 such that the distal end portion 20 enters a visual field (field angle AG10 in FIG. 7) of the optical adaptor 7 and also enters a focal range (focal range FR10 in FIG. 7) of the optical adaptor 7. The target state estimation unit 411 disposes the distal end portion 20 such that the state of the distal end portion 20 becomes the target state (Step SB100).

Figure 10:
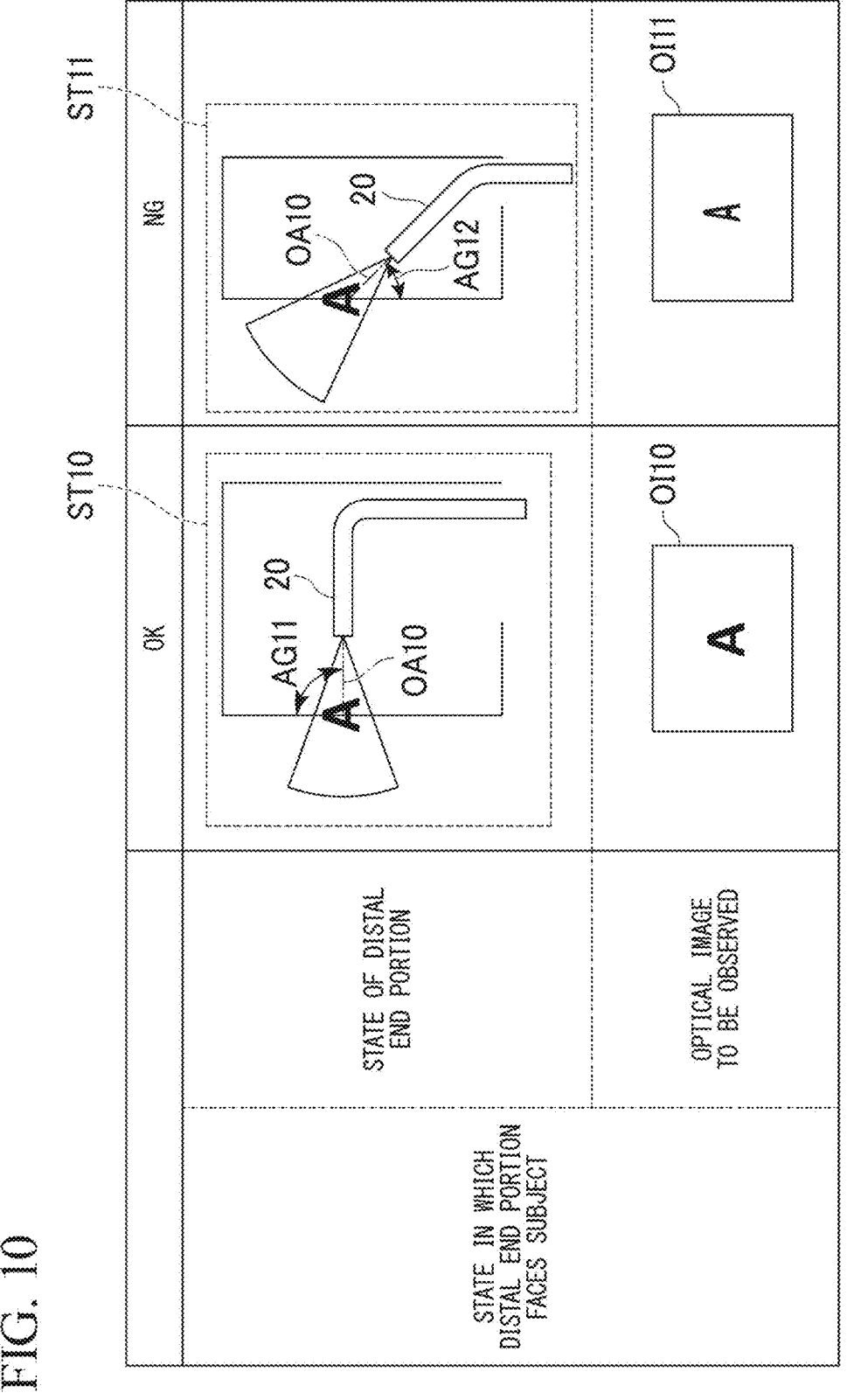
FIG. 10 is a diagram showing an example of a target state of a distal end portion of an insertion unit in the embodiment of the present invention.
Figure 11:
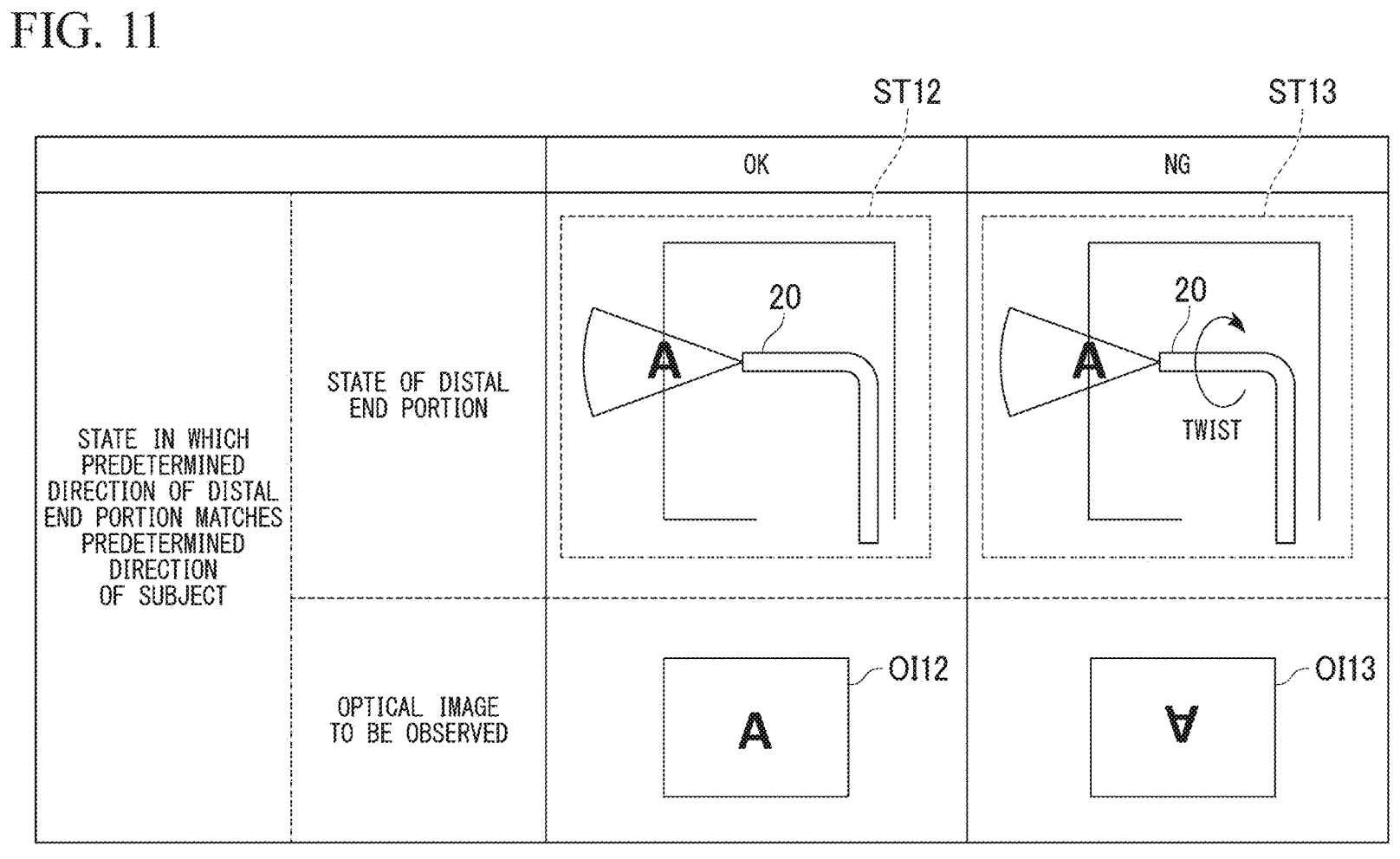
Figure 12:
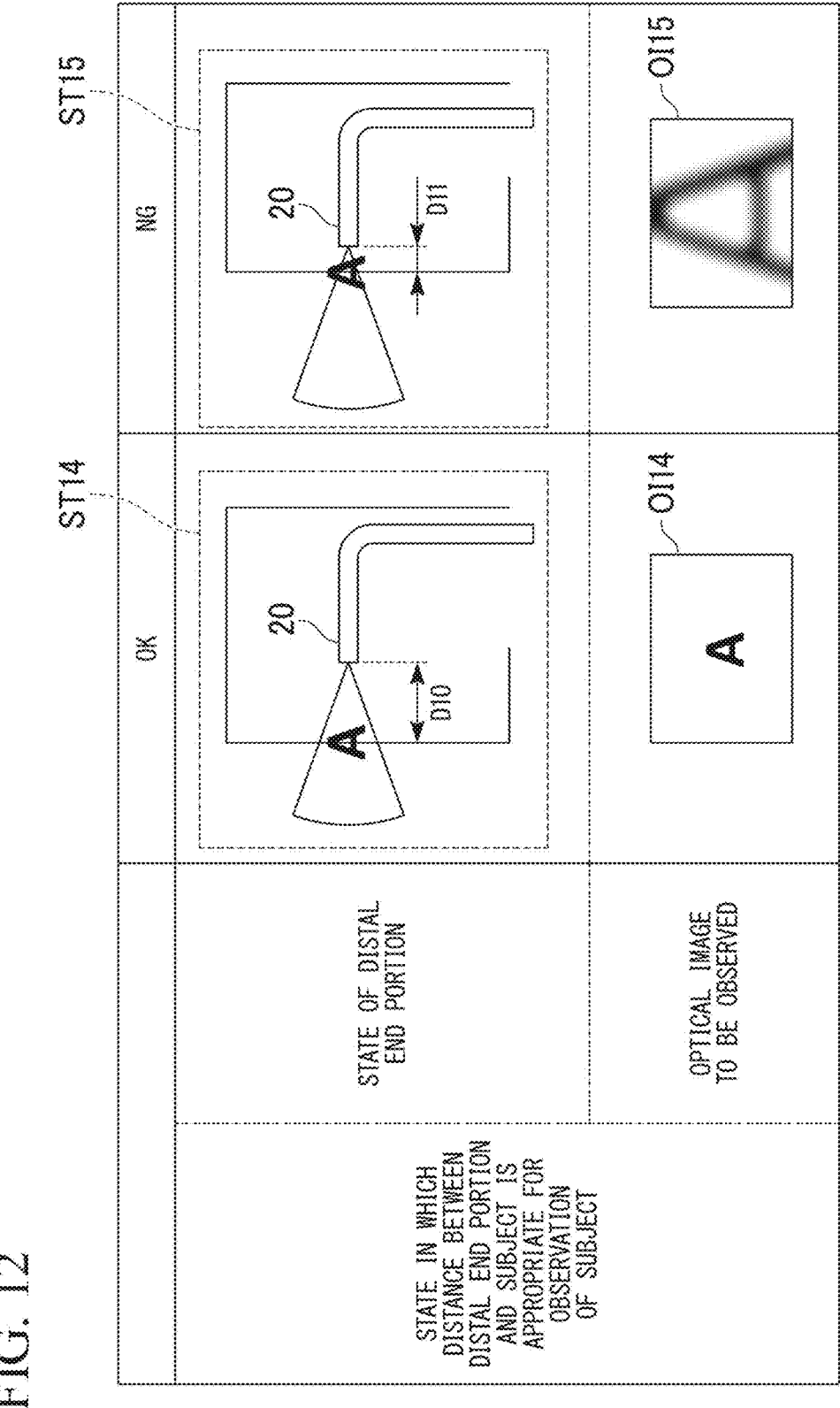
FIG. 12 is a diagram showing an example of a target state of the distal end portion of the insertion unit in the embodiment of the present invention.

FIG. 10, FIG. 11, and FIG. 12 show examples of the target state of the distal end portion 20.

FIG. 10 shows whether the distal end portion 20 faces the subject. In a state ST10 shown in FIG. 10, the distal end portion 20 faces the subject. At this time, the direction of an optical axis OA10 of the lens 22 disposed in the distal end portion 20 is perpendicular to the surface of the subject. In other words, an angle AG11 shown in FIG. 10 is at 90 degrees. The distal end portion 20 acquires an optical image OI10.

In a state ST11 shown in FIG. 10, the distal end portion 20 does not face the subject. At this time, the direction of the optical axis OA10 of the lens 22 disposed in the distal end portion 20 is not perpendicular to the surface of the subject. The distal end portion 20 acquires an optical image OI11.

The optical image OI10 is more appropriate for observation of the subject than the optical image OI11. The state ST10 is a target state, but the state ST11 is not the target state.

FIG. 11 shows whether a predetermined direction of the distal end portion 20 matches a predetermined direction of the subject. The predetermined direction of the distal end portion 20 is a direction set in the structure of the distal end portion 20 in advance. The predetermined direction of the subject is a direction set in the 3D shape of the subject in advance.

In a state ST12 shown in FIG. 11, the upward direction, the downward direction, the left direction, and the right direction of the distal end portion 20 match the upward direction, the downward direction, the left direction, and the right direction of the subject, respectively. The distal end portion 20 acquires an optical image OI12.

In a state ST13 shown in FIG. 11, the insertion unit 2 is twisted. Therefore, the upward direction of the distal end portion 20 matches the downward direction of the subject, and the downward direction of the distal end portion 20 matches the upward direction of the subject. The distal end portion 20 acquires an optical image OI13.

The optical image OI12 is more appropriate for observation of the subject than the optical image OI13. The state ST12 is a target state, but the state ST13 is not the target state.

FIG. 12 shows whether the distance between the distal end portion 20 and the subject is appropriate for observation of the subject. In a state ST14 shown in FIG. 12, the distance between the distal end portion 20 and the subject is D10. At this time, an inspection portion of the subject enters the field of view of the optical adaptor 7, and the focal direction of the optical adaptor 7 is suitable. The distal end portion 20 acquires an optical image OI14.

In a state ST15 shown in FIG. 12, the distance between the distal end portion 20 and the subject is D11. At this time, part of an inspection portion of the subject does not enter the field of view of the optical adaptor 7, and the focal direction of the optical adaptor 7 is unsuitable. The distal end portion 20 acquires an optical image OI15.

The optical image OI14 is more appropriate for observation of the subject than the optical image OI15. The state ST14 is a target state, but the state ST15 is not the target state.

The target state estimation unit 411 disposes the distal end portion 20 such that the state of the distal end portion 20 becomes a similar target state to at least one of the state ST10, the state ST12, and the state ST14. The target state does not need to be similar to all of the state ST10, the state ST12, and the state ST14. The target state may be similar to one or two of the state ST10, the state ST12, and the state ST14.

After Step SB100, the target state estimation unit 411 determines whether the disposition of the distal end portion 20 is obstructed by a wall of the subject (Step SB101).

When the target state estimation unit 411 determines that the disposition of the distal end portion 20 is obstructed by a wall of the subject in Step SB101, the target state estimation unit 411 outputs a message to the display unit 5 via the image-processing unit 30 (Step SB102). The message encourages a user to replace the optical adaptor 7 or notifies the user that it is impossible to perform an inspection.

When the target state estimation unit 411 determines that the disposition of the distal end portion 20 is not obstructed by a wall of the subject in Step SB101, the setting unit 410 sets the position at which the distal end portion 20 is disposed in Step SB100 as a final destination. In addition, the setting unit 410 sets the posture of the distal end portion 20 in Step SB100 as a target posture (Step SB103). When Step SB102 or Step SB103 is executed, the processing shown in FIG. 9 is completed.

Figure 13:
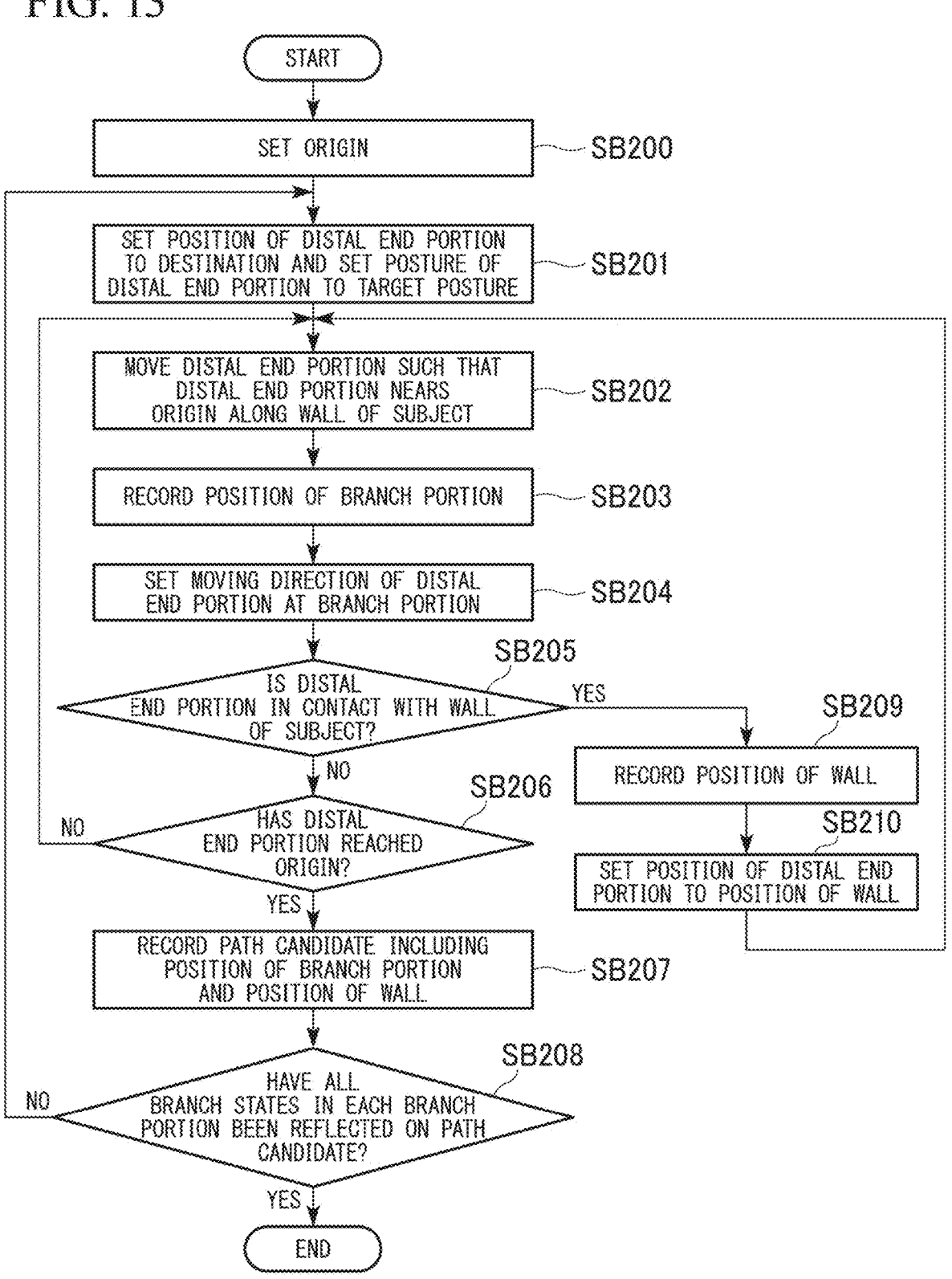
FIG. 13 is a flow chart showing a procedure of an operation of the endoscope device according to the embodiment of the present invention.

FIG. 13 shows processing executed in Step SB2 shown in FIG. 8. The setting unit 410 sets the origin indicated by the position information included in the subject information (Step SB200).

The path calculation unit 412 sets the position of the distal end portion 20 to the destination set in Step SB103. In this way, the path calculation unit 412 disposes the distal end portion 20 at the destination in the 3D shape of the subject. In addition, the path calculation unit 412 sets the posture of the distal end portion 20 to the target posture set in Step SB103 (Step SB201).

After Step SB201, the path calculation unit 412 moves the distal end portion 20 on the 3D shape such that the distal end portion 20 nears the origin along a wall of the subject (Step SB202).

In a case in which the distal end portion 20 passes through a branch portion, the path calculation unit 412 records the position of the branch portion (Step SB203). After Step SB203, the path calculation unit 412 sets a moving direction of the distal end portion 20 in accordance with the shape of the branch portion (Step SB204). In a case in which the distal end portion 20 does not pass through a branch portion, Step SB203 and Step SB204 are not executed.

After Step SB204, the path calculation unit 412 determines whether the distal end portion 20 is in contact with a wall of the subject (Step SB205).

When the path calculation unit 412 determines that the distal end portion 20 is in contact with a wall of the subject in Step SB205, the path calculation unit 412 records the position of the wall (Step SB209). After Step SB209, the path calculation unit 412 sets the position of the distal end portion 20 to the position of the wall (Step SB210). After Step SB210, Step SB202 is executed.

When the path calculation unit 412 determines that the distal end portion 20 is not in contact with a wall of the subject in Step SB205, the path calculation unit 412 determines whether the distal end portion 20 has reached the origin (Step SB206).

When the path calculation unit 412 determines that the distal end portion 20 has not reached the origin in Step SB206, Step SB202 is executed. When the path calculation unit 412 determines that the distal end portion 20 has reached the origin in Step SB206, the path calculation unit 412 records a path candidate including the position of the branch portion and the position of the wall (Step SB207).

After Step SB207, the path calculation unit 412 determines whether all the branch states at each branch portion have been reflected on the path candidate (Step SB208).

When the path calculation unit 412 determines that a branch state that has not been reflected on the path candidate remains in Step SB208, Step SB201 is executed. Thereafter, the path calculation unit 412 executes the processing described above and records a position of a branch portion and a position of a wall in a new path candidate. When the path calculation unit 412 determines that all the branch states have been reflected on the path candidate in Step SB208, the processing shown in FIG. 13 is completed.

Figure 14:
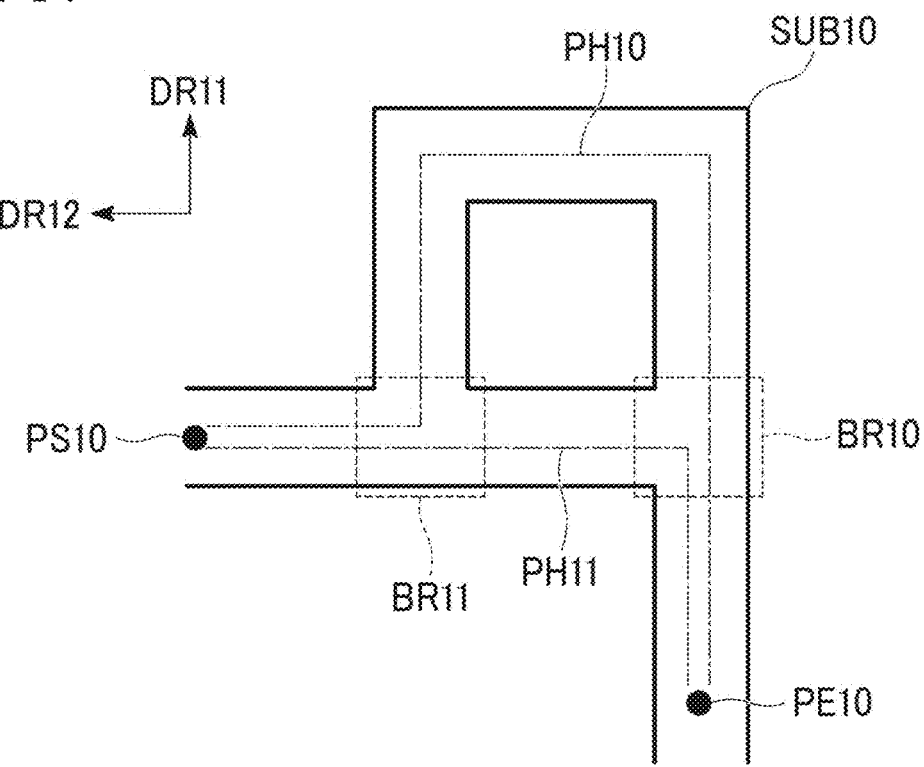
FIG. 14 is a diagram showing an example of a path candidate in the embodiment of the present invention.

FIG. 14 shows an example of the path candidate. An origin PS10 and a destination PE10 are set on a 3D shape SUB10 of a subject. The 3D shape SUB10 includes a branch portion BR10 and a branch portion BR1/. In FIG. 14, a path candidate PH10 and a path candidate PH11 are shown.

The path calculation unit 412 sets the position of the distal end portion 20 to the destination PE10 in Step SB201. The path calculation unit 412 moves the distal end portion 20 toward the origin PS10 in Step SB202.

Since the distal end portion 20 passes through the branch portion BR10, the path calculation unit 412 records the position of the branch portion BR10 in Step SB203.

The distal end portion 20 can move in a direction DR11 or a direction DR12 at the branch portion BR10. For example, the path calculation unit 412 sets the moving direction of the distal end portion 20 to the direction DR11 in Step SB204.

The path calculation unit 412 uses a branch management table for managing a state of branching at a branch portion. FIG. 15A, FIG. 15B, FIG. 15C, and FIG. 15D show an example of the branch management table. When the distal end portion 20 passes through the branch portion BR10, the path calculation unit 412 records a first branch state including the direction DR11 at the branch portion BR10 in the branch management table. FIG. 15A shows a branch management table TB10 at this time.

When the distal end portion 20 is in contact with a wall of the 3D shape SUB10, the path calculation unit 412 executes Step SB209 and Step SB210. Thereafter, the distal end portion 20 passes through the branch portion BR11. The path calculation unit 412 records the position of the branch portion BR11 in Step SB203. The distal end portion 20 can move in the direction DR12 at the branch portion BR11. The path calculation unit 412 sets the moving direction of the distal end portion 20 to the direction DR12 in Step SB204. At this time, the path calculation unit 412 associates the direction DR12 at the branch portion BR11 with the first branch state. FIG. 15B shows a branch management table TB11 at this time.

When the distal end portion 20 reaches the origin PS10, a branch state including the direction DR12 at the branch portion BR10 is not recorded in the branch management table TB11. Therefore, the path calculation unit 412 determines that a branch state that has not been reflected on the path candidate remains in Step SB208. The path calculation unit 412 sets the position of the distal end portion 20 to the destination PE10 in Step SB201 again. The path calculation unit 412 moves the distal end portion 20 toward the origin PS10 in Step SB202.

Since the distal end portion 20 passes through the branch portion BR10, the path calculation unit 412 records the position of the branch portion BR10 in Step SB203. Since the direction DR12 at the branch portion BR10 is not recorded in the branch management table TB11, the path calculation unit 412 sets the moving direction of the distal end portion 20 to the direction DR12 in Step SB204. At this time, the path calculation unit 412 records a second branch state including the direction DR12 at the branch portion BR10 in the branch management table. FIG. 15C shows a branch management table TB12 at this time.

Thereafter, the distal end portion 20 passes through the branch portion BR11. The path calculation unit 412 records the position of the branch portion BR11 in Step SB203. The path calculation unit 412 sets the moving direction of the distal end portion 20 to the direction DR12 in Step SB204. At this time, the path calculation unit 412 associates the direction DR12 at the branch portion BR11 with the second branch state. FIG. 15D shows a branch management table TB13 at this time.

When the distal end portion 20 reaches the origin PS10, the branch management table TB13 stores information of all the branch states related to the branch portion BR10 and the branch portion BR11. Therefore, the path calculation unit 412 determines that all the branch states have been reflected on the path candidate in Step SB208.

Figure 16:
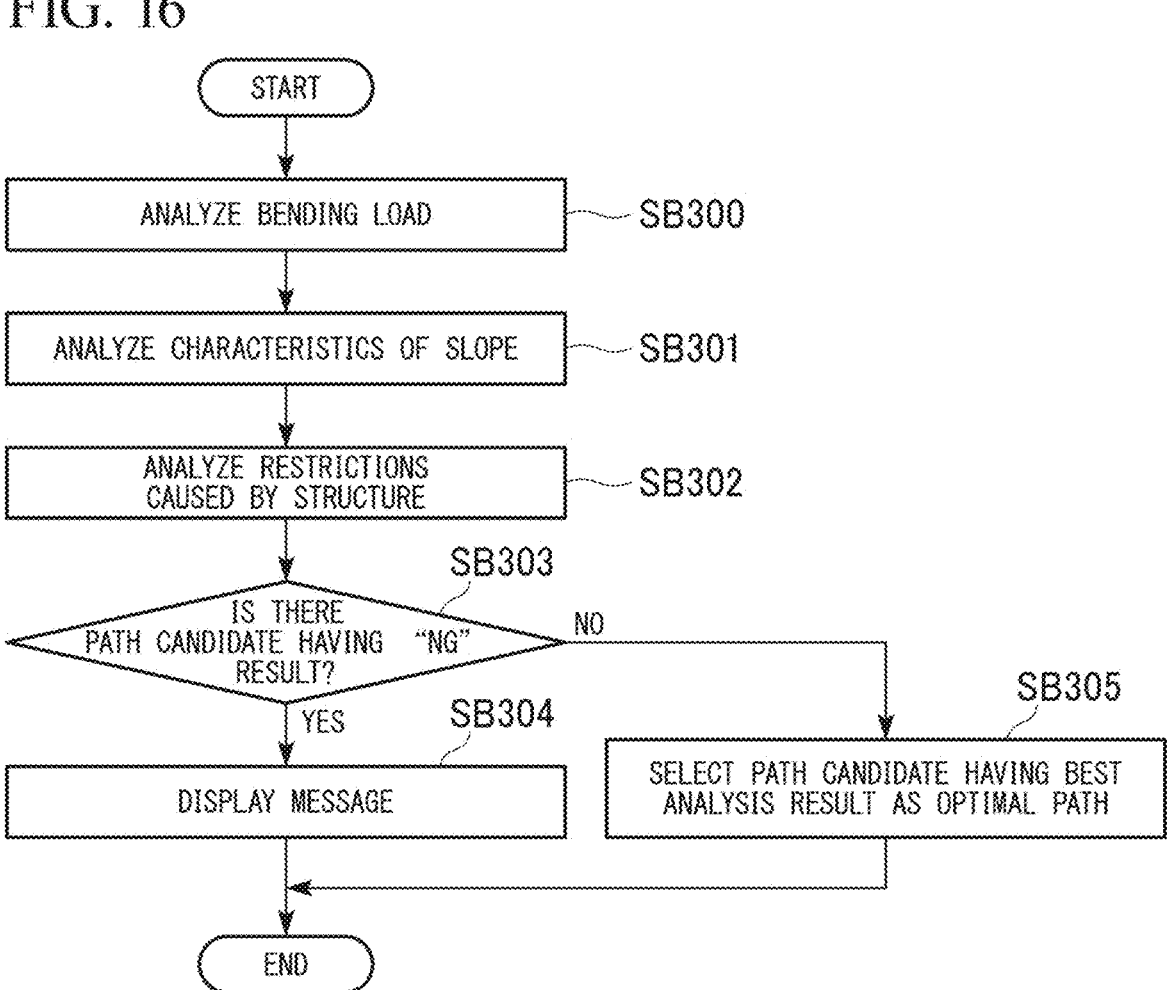
FIG. 16 is a flow chart showing a procedure of an operation of the endoscope device according to the embodiment of the present invention.

FIG. 16 shows processing executed in Step SB3 shown in FIG. 8. The path calculation unit 412 analyzes a bending load of the insertion unit 2 in each path candidate (Step SB300).

When the insertion unit 2 is bent, a friction force between a subject and the insertion unit 2 increases. The friction force adds a bending load onto the insertion unit 2 when the insertion unit 2 is inserted into the subject. Therefore, it is difficult for a user to insert the insertion unit 2 into the subject. As the amount of the insertion unit 2 being bent increases, the bending load increases.

Figure 17A:
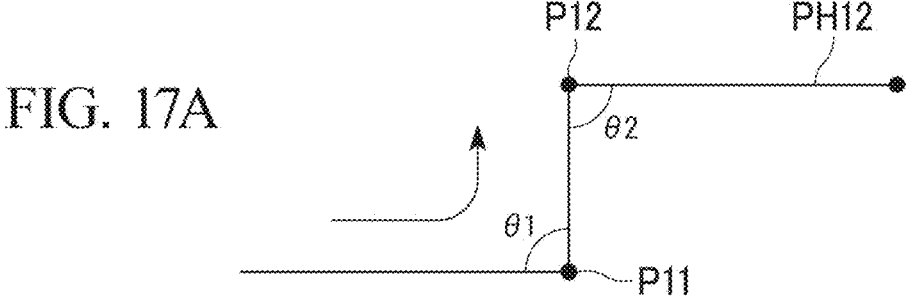
FIG. 17A is a diagram showing a method of calculating an amount of a bending load of the insertion unit in the embodiment of the present invention.
Figure 17B:
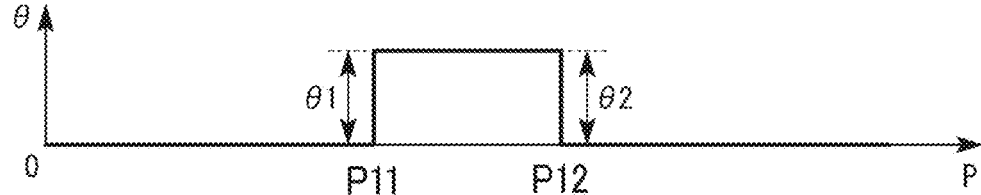
FIG. 17B is a diagram showing a method of calculating an amount of a bending load of the insertion unit in the embodiment of the present invention.
Figure 17C:
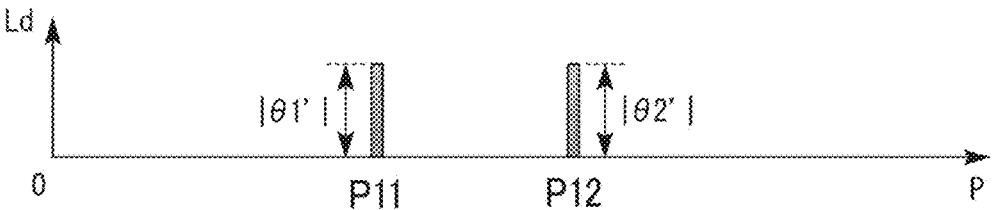
FIG. 17C is a diagram showing a method of calculating an amount of a bending load of the insertion unit in the embodiment of the present invention.

FIG. 17A, FIG. 17B, and FIG. 17C show a method of calculating the amount of the bending load of the insertion unit 2. FIG. 17A shows an example of the path candidate. A path candidate PH12 shown in FIG. 17A turns by an angle θ1 at a position P11 and turns by an angle θ2 at a position P12. The angle θ1 and the angle θ2 are at 90 degrees.

FIG. 17B shows a change of the bending amount of the insertion unit 2. The horizontal axis in FIG. 17B indicates a position P in the path candidate PH12, and the vertical axis in FIG. 17B indicates the bending amount of the insertion unit 2. The bending amount of the insertion unit 2 is shown as an angle θ.

FIG. 17C shows the amount of the bending load. The horizontal axis in FIG. 17C indicates a position P in the path candidate PH12, and the vertical axis in FIG. 17C indicates an amount Ld of the bending load. The path calculation unit 412 calculates a derivative value of a change of the bending amount shown in FIG. 17B and calculates an absolute value of the derivative value as the amount Ld of the bending load. At this time, the path calculation unit 412 uses the shape information of a subject. The path calculation unit 412 can calculate the amount of a sharp and large bend.

The path calculation unit 412 calculates a sum of the absolute values of the derivative values for each path candidate. The sum indicates the amount of the bending load for each path candidate. When the amount of the bending load is very large, the path calculation unit 412 determines that the path candidate is unavailable. When the amount of the bending load is small, the path calculation unit 412 determines that the path candidate is available.

After Step SB300, the path calculation unit 412 analyzes characteristics of a slope included in a path in each path candidate (Step SB301).

Figure 18A:
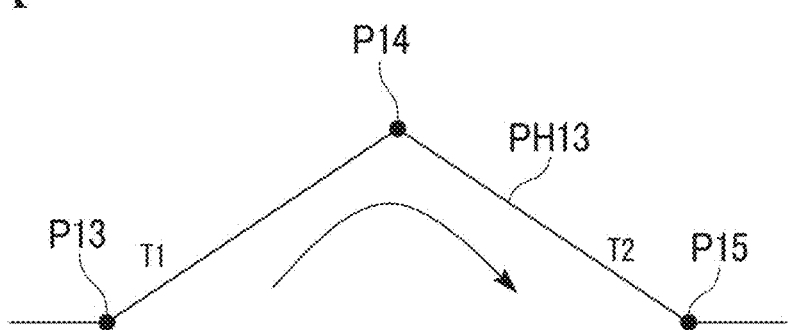
FIG. 18A is a diagram showing a method of analyzing characteristics of a slope of the path candidate in the embodiment of the present invention.
Figure 18B:
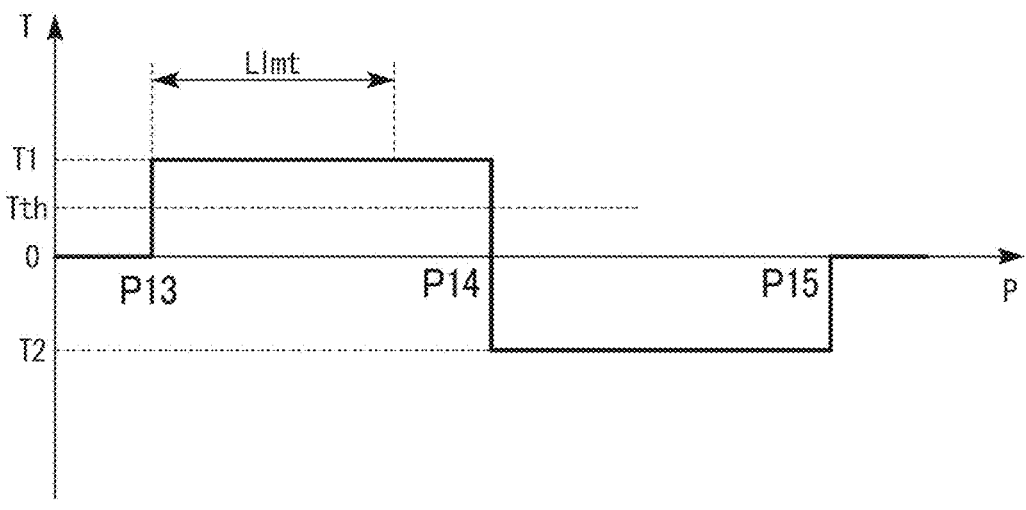
FIG. 18B is a diagram showing a method of analyzing characteristics of a slope of the path candidate in the embodiment of the present invention.

FIG. 18A and FIG. 18B show a method of analyzing characteristics of a slope. FIG. 18A shows characteristics of a slope of a path candidate PH13. In FIG. 18A, a change of height of the path candidate PH13 is shown. The path candidate PH13 ascends from a position P13 to a position P14 and descends from the position P14 to a position P15. The gradient of the slope from the position P13 to the position P14 is T1, and the gradient of the slope from the position P14 to the position P15 is T2.

FIG. 18B shows a change of the gradient of the slope in the path candidate PH13. The horizontal axis in FIG. 18B indicates a position P in the path candidate PH13, and the vertical axis in FIG. 18B indicates a gradient T of a slope.

In a case in which the gradient of an ascending slope is large and the slope is long, a force required for moving the insertion unit 2 is large. The path calculation unit 412 determines whether the gradient of the slope is greater than a threshold value Tth and the length of the slope is longer than a threshold value Llmt. At this time, the path calculation unit 412 uses the shape information of a subject. In the example shown in FIG. 18B, the gradient T1 is greater than the threshold value Tth. In addition, the length of the slope having the gradient T1 is longer than the threshold value Llmt. Therefore, the path calculation unit 412 determines that the path candidate PH13 is unavailable.

The path calculation unit 412 calculates the gradient of a slope in each path candidate. When the gradient is greater than the threshold value Tth and the length of the slope having the gradient is longer than the threshold value Llmt, the path calculation unit 412 determines that the path candidate is unavailable. When the gradient of the slope is less than or equal to the threshold value Tth or the length of the slope having a gradient greater than the threshold value Tth is less than or equal to the threshold value Unit, the path calculation unit 412 determines that the path candidate is available.

Most of the insertion unit 2 excluding the rigid portion is flexible and is easy to bend. When the insertion unit 2 is ascending a slope, the direction of the distal end portion 20 tends to change to the left or right and the insertion unit 2 is likely to topple down. In a case in which there is not a wall or the like on both sides of the insertion unit 2 to restrict the insertion unit 2 from toppling down, there is a possibility that the insertion unit 2 cannot ascend the slope. The path calculation unit 412 may determine whether the path candidate is available on the basis of the distance between the insertion unit 2 and a wall or the like of a subject.

After Step SB301, the path calculation unit 412 analyzes restrictions on the disposition of the insertion unit 2 caused by the structure of a subject in each path candidate and the structure of the insertion unit 2 (Step SB302).

The order of Step SB301, Step SB302, and Step SB303 is not limited to that shown in FIG. 16. Step SB301, Step SB302, and Step SB303 may be executed in any order.

Figure 19:
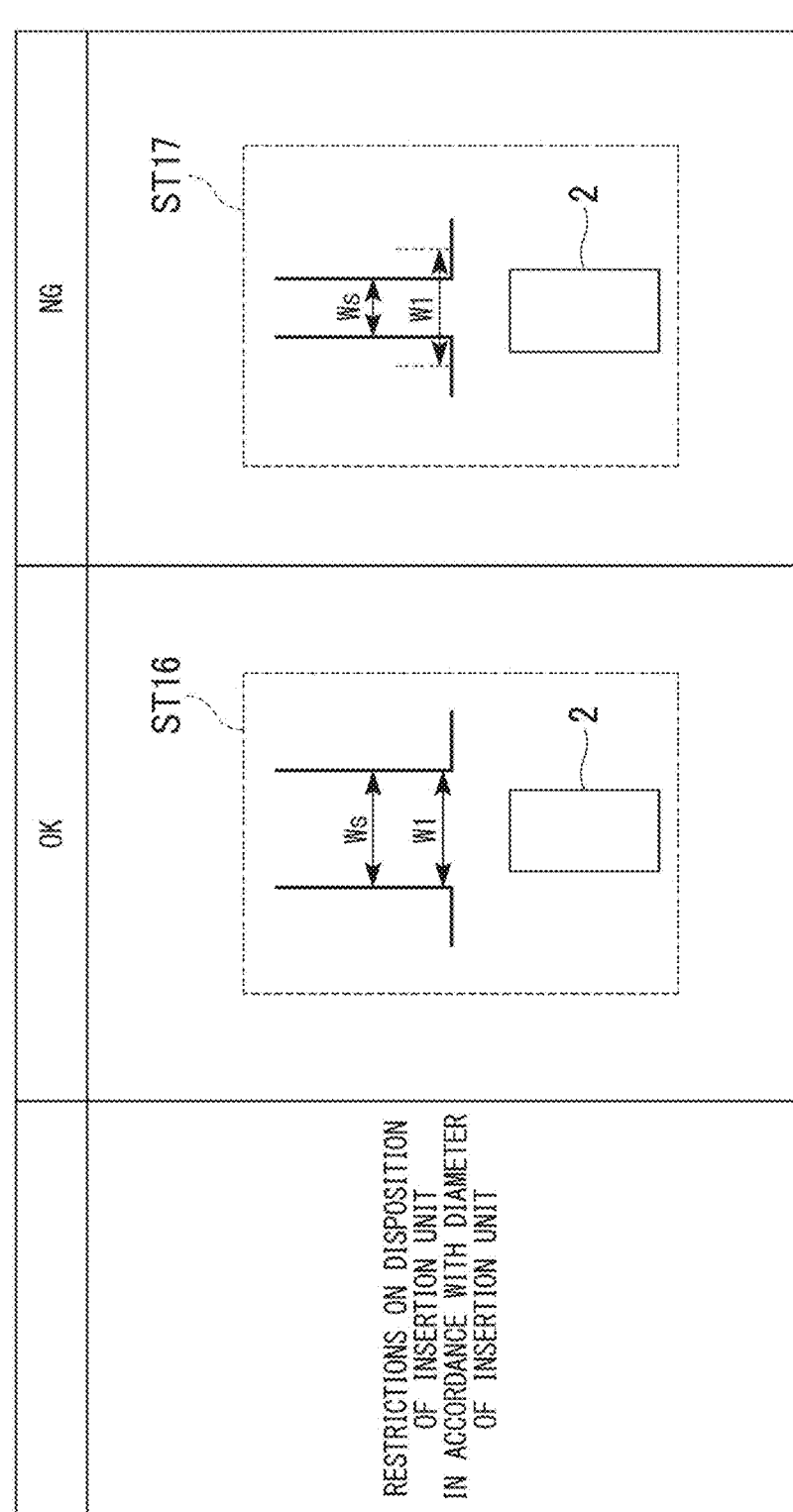
FIG. 19 is a diagram showing an example of restrictions on the disposition of the insertion unit in accordance with the diameter of the insertion unit in the embodiment of the present invention.
Figure 21:
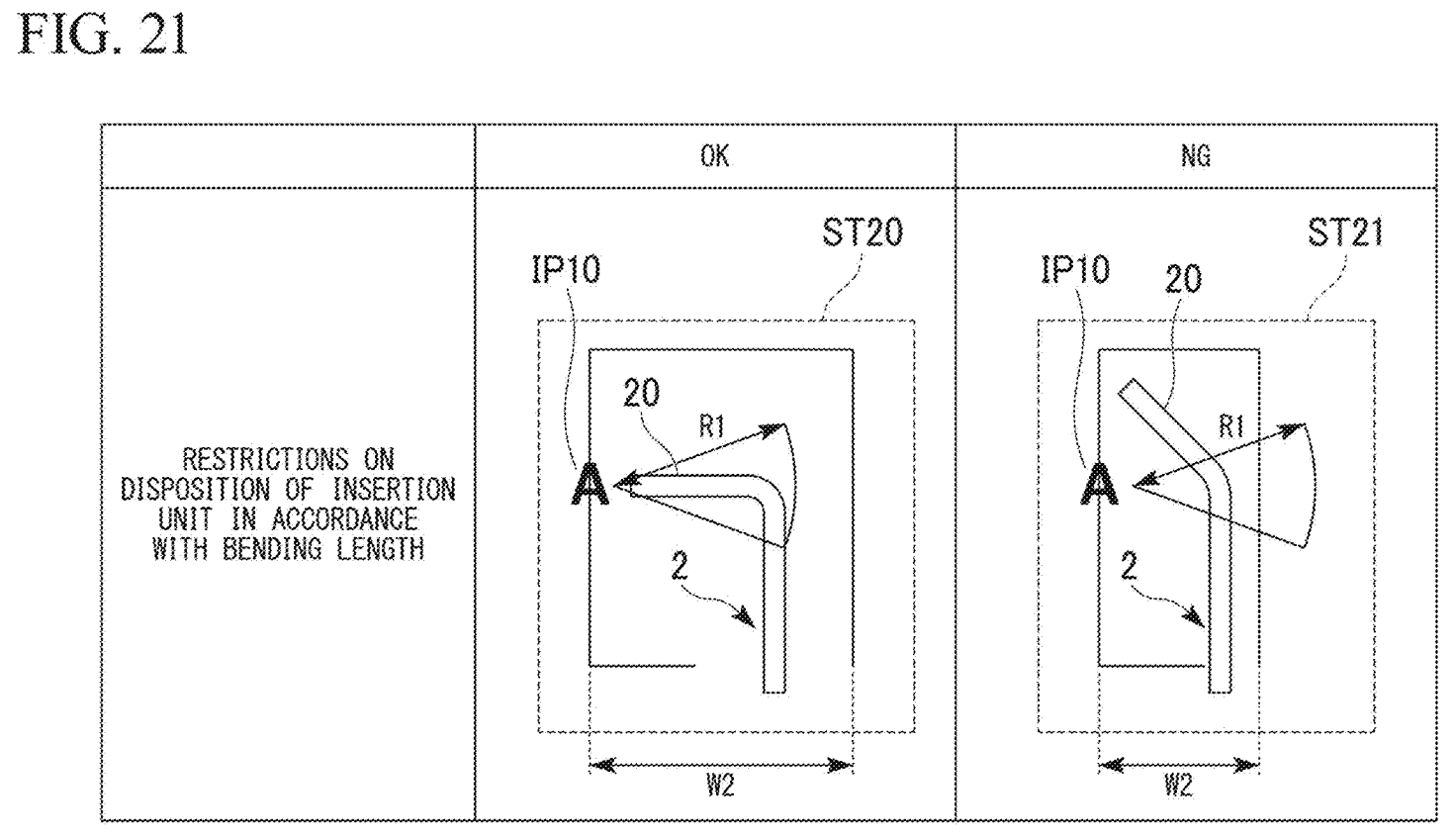

FIG. 19, FIG. 20, and FIG. 21 show examples of restrictions on the disposition of the insertion unit 2 caused by the structure of a subject and the structure of the insertion unit 2.

FIG. 19 shows an example of restrictions on the disposition of the insertion unit 2 in accordance with the diameter of the insertion unit 2. In a state ST16 shown in FIG. 19, a width Ws of a space in a subject into which the insertion unit 2 is inserted is the same as W1. A width W1 indicates a necessary width of the space in the subject for the insertion unit 2 to pass through the space. The width W1 is greater than or equal to the diameter of the insertion unit 2. The insertion unit 2 can pass through the space in the subject in the state ST16.

In a state ST17 shown in FIG. 19, the width Ws of a space in a subject into which the insertion unit 2 is inserted is less than W1. The insertion unit 2 cannot pass through the space in the subject in the state ST17.

The path calculation unit 412 calculates the width W1 by using the insertion unit information. The path calculation unit 412 calculates the width Ws of a space in each path candidate by using the shape information of a subject. The path calculation unit 412 determines whether the width Ws is greater than or equal to the width W1. When the width Ws is less than the width W1, the path calculation unit 412 determines that the path candidate is unavailable. When the width Ws is greater than or equal to the width W1, the path calculation unit 412 determines that the path candidate is available.

FIG. 20 shows an example of restrictions on the disposition of the insertion unit 2 in accordance with the length of the rigid portion of the insertion unit 2. In a state ST18 shown in FIG. 20, the minimum value Wm of the width in a bent part of a subject is greater than or equal to r1. The width r1 indicates a necessary width of a bent part for the rigid portion of the distal end portion 20 to pass through the bent part. The insertion unit 2 can pass through the bent part in the state ST18.

In a state ST19 shown in FIG. 20, the minimum value Wm of the width in a bent part of a subject is less than r1. The insertion unit 2 cannot pass through the bent part in the state ST19.

The path calculation unit 412 calculates the width r1 by using the insertion unit information. The path calculation unit 412 calculates the minimum value Wm of the width of a bent part in each path candidate by using the shape information of a subject. The path calculation unit 412 determines whether the minimum value Wm is greater than or equal to the width r1. When the minimum value Wm is less than the width r1, the path calculation unit 412 determines that the path candidate is unavailable. When the minimum value Wm is greater than or equal to the width r1, the path calculation unit 412 determines that the path candidate is available.

FIG. 21 shows an example of restrictions on the disposition of the insertion unit 2 in accordance with the bending length of the insertion unit 2. In a state ST20 shown in FIG. 21, a length W2 between walls of a subject is greater than or equal to a distance R1. The distance R1 indicates a necessary interval of walls for the insertion unit 2 to acquire an optical image of an inspection portion IP10 in a state in which the insertion unit 2 is bent. The distance R1 is greater than or equal to the bending length. The distal end portion 20 of the insertion unit 2 can face the inspection portion IP10 in the state ST20.

In a state ST21 shown in FIG. 21, a distance W2 between walls of a subject is less than the distance R1. The distal end portion 20 of the insertion unit 2 cannot face the inspection portion IP10 in the state ST21.

The path calculation unit 412 calculates the distance R1 by using the insertion unit information. The path calculation unit 412 calculates the distance W2 in each path candidate by using the shape information of a subject. The path calculation unit 412 determines whether the distance W2 is greater than or equal to the distance R1. When the distance W2 is less than the distance R1, the path calculation unit 412 determines that the path candidate is unavailable. When the distance W2 is greater than or equal to the distance R1, the path calculation unit 412 determines that the path candidate is available.

After Step SB302, the path calculation unit 412 refers to an analysis result of each path candidate in each of Steps SB300 to SB302. The path calculation unit 412 determines whether there is a path candidate determined to be unavailable (Step SB303).

When the path calculation unit 412 determines that there is no path candidate determined to be unavailable in Step SB303, the path calculation unit 412 selects a path candidate having the best analysis result as an optimal path (Step SB305).

When the path calculation unit 412 determines that there is a path candidate determined to be unavailable in Step SB303, the path calculation unit 412 outputs a message to the display unit 5 via the image-processing unit 30 (Step SB304). The message encourages a user to replace the endoscope device 1 or notifies the user that it is impossible to perform an inspection. When Step SB304 or Step SB305 is executed, the processing shown in FIG. 16 is completed.

Figures 22, 23:
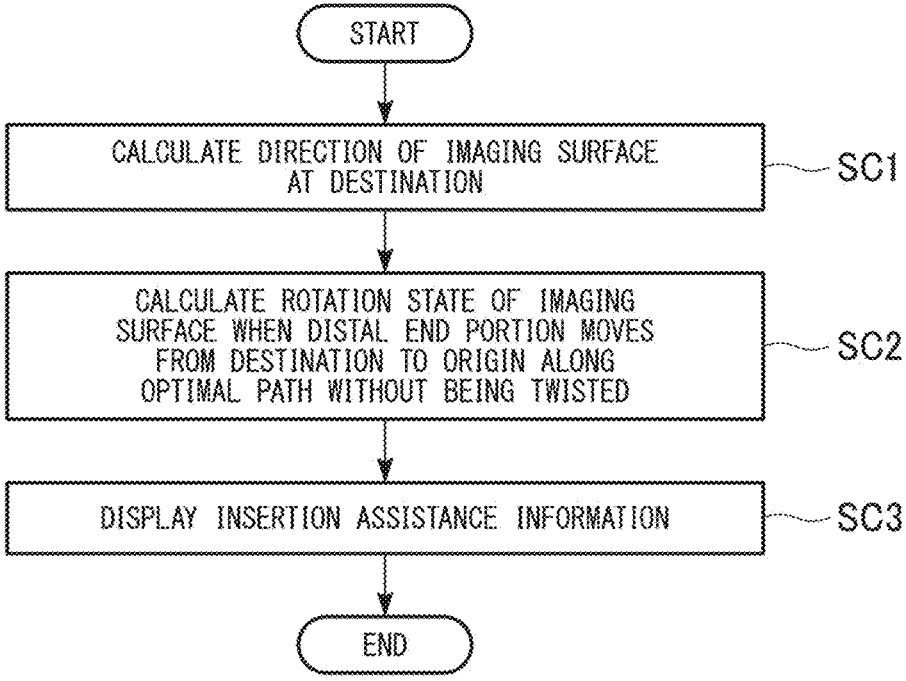
FIG. 22 is a diagram showing an example of an analysis result of the path candidate in the embodiment of the present invention.
FIG. 23 is a flow chart showing a procedure of an operation of the endoscope device according to the embodiment of the present invention.

FIG. 22 shows an example of the analysis result of each path candidate in each of Steps SB300 to SB302. The analysis result of each path candidate includes the analysis result of the bending load in Step SB300, the analysis result of the characteristics of the slope in Step SB301, and the analysis result of the restrictions on the disposition of the insertion unit 2 in Step SB302. Each analysis result is any one of a result A, a result B, and a result C. The result A indicates that the path candidate is good. The result B indicates that the analysis result is not classified into the result A but the path candidate is available. The result C indicates that the path candidate is unavailable.

The analysis result of each of path candidates 1 to 4 is shown in FIG. 22. In addition, the total length (path length) of each path candidate is shown in FIG. 22. The path calculation unit 412 determines whether there is a path candidate having the result C in Step SB303.

The analysis result of the bending load of the path candidate 1 is the result C. The analysis result of the restrictions of the path candidate 2 is the result C. The analysis result of the characteristics of the slope of the path candidate 3 is the result C. Therefore, the path calculation unit 412 does not select the path candidates 1 to 3 as an optimal path. The path candidate 4 does not have the result C. Therefore, the path calculation unit 412 selects the path candidate 4 as the optimal path.

In a case in which there are two or more path candidates determined to be unavailable, the path calculation unit 412 may select a path candidate having a relatively good analysis result as the optimal path. Alternatively, the path calculation unit 412 may select a path candidate having the shortest path length as the optimal path.

In the above-described examples, the path calculation unit 412 analyzes each path candidate in accordance with two or more indices related to at least one of the insertion unit 2 and a subject. In the above-described examples, a first index, a second index, and a third index are used. The first index is related to a load added on the insertion unit 2 when the insertion unit 2 is bent on each path candidate. The second index is related to characteristics of a slope in each path candidate. The third index is related to restrictions on the disposition of the insertion unit 2 caused by the structure of each of the insertion unit 2 and the subject. The path calculation unit 412 may analyze each path candidate in accordance with only one index.

For example, the path calculation unit 412 executes the following processing. The path calculation unit 412 analyzes each path candidate in accordance with each index and calculates an index value in accordance with the analysis result. For example, the index value of the result A shown in FIG. 22 is 2, the index value of the result B shown in FIG. 22 is 1, and the index value of the result C shown in FIG. 22 is 0. For example, the path calculation unit 412 calculates a sum SUM of the three index values of each path candidate by using the following Expression (1).

$$SUM = I1 + I2 + I3 \qquad (1)$$

A value I1 in Expression (1) indicates the value of the first index. A value I2 in Expression (1) indicates the value of the second index. A value I3 in Expression (1) indicates the value of the third index. The path calculation unit 412 selects a path candidate having the smallest sum SUM as the optimal path.

A weight coefficient may be set in each index in accordance with the degree of importance of each index. The path calculation unit 412 may analyze each path candidate in accordance with each index and the weight coefficient. For example, the weight coefficient of each index indicates whether the index is used in order to select the optimal path. For example, the weight coefficient of the first index is 1, the weight coefficient of the second index is 1, and the weight coefficient of the third index is 0. In this case, the first index and the second index are used to select the optimal path, but the third index is not used to select the optimal path.

The path calculation unit 412 may execute the following processing. The path calculation unit 412 multiplies each index value by the weight coefficient of each index, thus calculating a corrected index value. The path calculation unit 412 calculates a sum of the three corrected index values of each path candidate. For example, the path calculation unit 412 calculates a sum SUM of the three corrected index values of each path candidate by using the following Expression (2).

$$SUM = C1*I1 + C2*I2 + C3*I3 \qquad (2)$$

A value C1 in Expression (2) indicates a weight coefficient of the first index, and a value I1 indicates a value of the first index. A value C2 in Expression (2) indicates a weight coefficient of the second index, and a value I2 indicates a value of the second index. A value C3 in Expression (2) indicates a weight coefficient of the third index, and a value I3 indicates a value of the third index. The path calculation unit 412 selects a path candidate having the smallest sum SUM as the optimal path.

The above-described weight coefficient is stored on the memory 43 in advance. The weight coefficient may be variable. For example, a user may input the weight coefficient into the endoscope device 1 by operating the operation unit 4. The weight coefficient stored on the memory 43 may be changed to the weight coefficient input into the endoscope device 1.

FIG. 23 shows processing executed in Step SC shown in FIG. 4. The insertion assistance unit 42 calculates a direction of the imaging surface 23a of the imaging device 23 in a state in which the distal end portion 20 is disposed at the destination (Step SC1). At this time, the posture of the distal end portion 20 is set to the target posture.

Figures 24, 25:
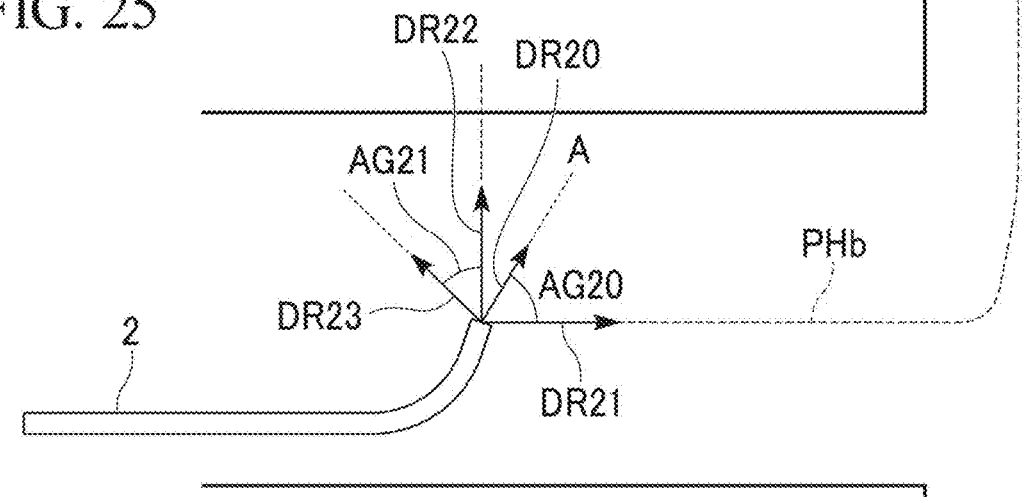
FIG. 24 is a diagram showing an example of a model of a path in the embodiment of the present invention.
FIG. 25 is a diagram showing a state of the insertion unit when insertion assistance information is generated in the embodiment of the present invention.

FIG. 24 shows a model of a path. When the distal end portion 20 is disposed at the destination, the distal end portion 20 acquires an optical image of an inspection portion IP11. Since the posture of the distal end portion 20 is set to the target posture, the distal end portion 20 faces the inspection portion IP11.

A vector Ua and a vector Va shown in FIG. 24 are defined. The vector Ua is parallel to the surface of the inspection portion IP11 and matches a reference direction. For example, the reference direction is defined as the upward direction in the inspection portion IP11. The vector Va is perpendicular to the surface of the inspection portion IP11. The vector Ua and the vector Va are defined by a global coordinate system in a subject. The global coordinate system has an X-axis, a Y-axis, and a Z-axis. A position (3D coordinates) in the global coordinate system is defined by the X-axis, the Y-axis, and the Z-axis.

On the other hand, a local coordinate system in the imaging surface 23$a$ of the imaging device 23 is defined. The local coordinate system has an x-axis, a y-axis, and a z-axis. The direction of the x-axis is the same as the horizontal direction in the imaging surface 23$a$, and the direction of the y-axis is the same as the vertical direction in the imaging surface 23$a$. The direction of the z-axis is perpendicular to the imaging surface 23$a$. A position (3D coordinates) in the local coordinate system is defined by the x-axis, the y-axis, and the z-axis.

When the distal end portion 20 is disposed at the destination, the imaging surface 23$a$ faces the inspection portion IP11 and the upward direction of the imaging surface 23$a$ matches the upward direction of the inspection portion IP11. Therefore, the direction of the z-axis of the local coordinate system matches the direction of the vector Va, and the direction of the y-axis of the local coordinate system matches the direction of the vector Ua.

After Step SC1, the insertion assistance unit 42 calculates a rotation state of the imaging surface 23$a$ when the distal end portion 20 moves from the destination to the origin along the optimal path without being twisted (Step SC2).

A unit vector i is set on the z-axis of the local coordinate system. The direction of the unit vector i matches the direction of the z-axis. The direction of the unit vector i indicates a moving direction of the insertion unit 2. When the distal end portion 20 is disposed at the destination, the unit vector i is parallel to the vector Va.

The insertion assistance unit 42 calculates a rotation amount of the unit vector i when the distal end portion 20 passes through a bending position. The bending position indicates a position of a branch portion of a subject or a position of a wall of the subject. The insertion assistance unit 42 calculates a unit vector $i_0$ before the distal end portion 20 passes through the bending position. In addition, the insertion assistance unit 42 calculates a unit vector $i_1$ after the distal end portion 20 passes through the bending position. At this time, the insertion assistance unit 42 calculates each unit vector as a value in the global coordinate system by using the shape information of the subject.

The insertion assistance unit 42 uses a relationship between the unit vector i and a rotation matrix in order to calculate the rotation amount of the unit vector i at the bending position. The insertion assistance unit 42 calculates a rotation amount $\theta_1$ of the unit vector i by using a method such as a least-squares method. The rotation amount $\theta_1$ is expressed as a matrix in the global coordinate system. The insertion assistance unit 42 converts the rotation amount in the global coordinate system into a rotation amount in the local coordinate system. At this time, a condition ($\varphi=0$)

indicating that the unit vector i does not rotate around the z-axis is used. The unit vector i can rotate around the x-axis or the y-axis.

The insertion assistance unit 42 repeats the above-described processing until the distal end portion 20 reaches the origin. The insertion assistance unit 42 calculates a unit vector $i_2$ and the like and calculates a rotation amount $\theta_2$ and the like. When the distal end portion 20 is disposed at the origin, the distal end portion 20 acquires an optical image of an inspection portion IP12.

A vector Ub and a vector Vb shown in FIG. 24 are defined. The vector Ub is parallel to the surface of the inspection portion IP12 and matches a reference direction. For example, the reference direction is defined as the upward direction in the inspection portion IP12. The vector Vb is perpendicular to the surface of the inspection portion IP12. The vector Ub and the vector Vb are defined by the global coordinate system. When the unit vector i at the origin matches the vector Vb, the insertion assistance unit 42 determines that the distal end portion 20 reaches the origin.

The insertion assistance unit 42 calculates a sum of rotation amounts in the global coordinate system by using the rotation amount of the unit vector i at each bending position between the origin and the destination. In this way, the insertion assistance unit 42 calculates a rotation state of the imaging surface 23$a$ at the origin. The rotation state indicates the posture of the distal end portion 20 at the origin.

The unit vector i does not rotate around the z-axis at each bending position. In a case in which the above-described rotation state of the imaging surface 23$a$ at the origin is realized, the distal end portion 20 moves from the origin to the destination without the insertion unit 2 rotating around the z-axis.

The insertion operation of the insertion unit 2 mainly includes an operation of pushing or pulling the insertion unit 2 in the longitudinal direction of the insertion unit 2, an operation of twisting the insertion unit 2, and an operation of bending the bending portion 21. Since these operations are performed, the insertion operation is complicated and a user needs to be proficient in the operations. In a case in which a portion of the insertion unit 2 inserted in a subject is long, a great force is required for the operation of twisting the insertion unit 2. Therefore, work of a user is troublesome. The insertion assistance unit 42 calculates an ideal rotation state of the imaging surface 23$a$ at the origin in order to restrict implementation of the operation of twisting the insertion unit 2 in Step SC2.

After Step SC2, the insertion assistance unit 42 generates insertion assistance information on the basis of the position and the posture of the distal end portion 20 determined by the state determination unit 40, the optimal path calculated by the path-processing unit 41, and the shape information included in the subject information. The insertion assistance unit 42 outputs the insertion assistance information to the display unit 5 via the image-processing unit 30 and displays the insertion assistance information on the display unit 5 (Step SC3). When Step SC3 is executed, the processing shown in FIG. 23 is completed.

The insertion assistance unit 42 executes the following processing in Step SC3. FIG. 25 shows a state of the insertion unit 2 when the insertion assistance information is generated. The insertion assistance unit 42 calculates the amount of an angle AG20 between a present direction DR20 of the distal end portion 20 and a direction DR21 of an optimal path PHb. The present direction DR20 of the distal end portion 20 is indicated by the posture of the distal end portion 20 determined by the state determination unit 40. The direction DR21 of the optimal path PHb is indicated by the optimal path and the shape information. The insertion assistance unit 42 generates an image of an arrow indicating both the direction DR21 of the optimal path PHb and the amount of the angle AG20 and displays the image on the display unit 5. The image is included in the insertion assistance information.

Figure 26:
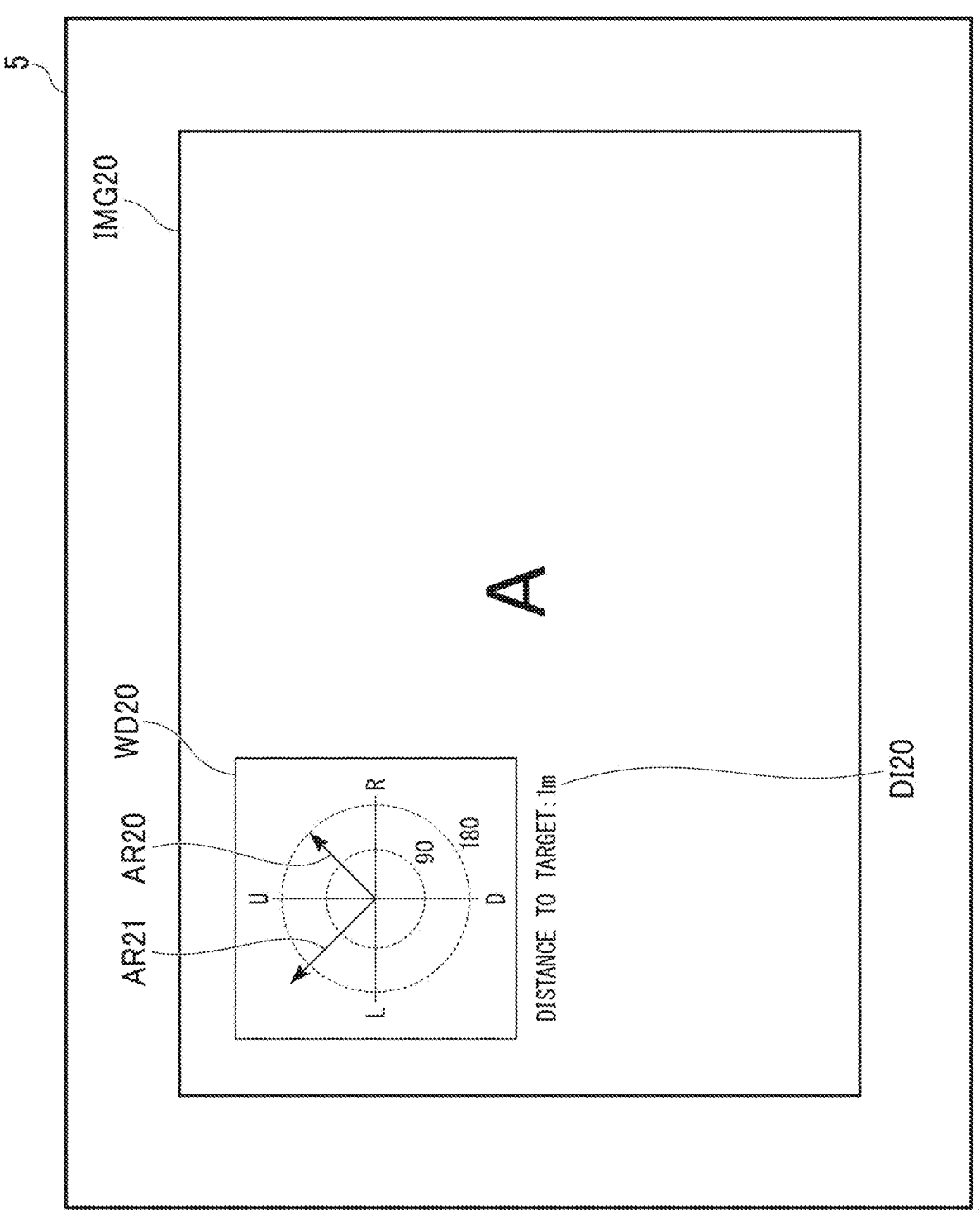
FIG. 26 is a diagram showing an example of the insertion assistance information displayed on a display unit in the embodiment of the present invention.

FIG. 26 shows an example of the insertion assistance information displayed on the display unit 5. The display unit 5 displays an image IMG 20 processed by the image-processing unit 30. A window WD20 for assisting the insertion operation is displayed on the image IMG 20. An arrow AR20 is displayed in the window WD20. The length of the arrow AR20 indicates the amount of the angle AG20. The angle AG20 ranges from 0 to 180 degrees. When the angle AG20 is at 180 degrees, the arrow AR20 is the longest.

The direction of the arrow AR20 indicates the direction of the optimal path PHb in the imaging surface 23a of the imaging device 23. In general, the endoscope device 1 is designed such that the upward direction, the downward direction, the left direction, and the right direction of the imaging surface 23a match the upward direction, the downward direction, the left direction, and the right direction of the bending operation, respectively. For example, a user tilts a joystick of the operation unit 4 in the direction of the arrow AR20. In this way, the distal end portion 20 faces in the direction DR21 of the optimal path PHb.

The insertion assistance unit 42 calculates the amount of an angle AG21 between an optimal upward direction DR22 of the imaging surface 23a and a present upward direction DR23 of the imaging surface 23a. The optimal upward direction DR22 of the imaging surface 23a is calculated in Step SC2. The present upward direction DR23 of the imaging surface 23a is indicated by the posture of the distal end portion 20 determined by the state determination unit 40. The insertion assistance unit 42 generates an image of an arrow indicating the amount of the angle AG21 and displays the image on the display unit 5. The image is included in the insertion assistance information.

An arrow AR21 is displayed in the window WD20. The direction of the arrow AR21 indicates the amount of the angle AG21. When the arrow AR21 faces in the upward direction in the display screen of the display unit 5, the twist state of the insertion unit 2 is ideal. A user twists the insertion unit 2 such that the arrow AR21 faces in the upward direction.

The insertion assistance unit 42 calculates the distance between the position of the distal end portion 20 determined by the state determination unit 40 and the destination of the optimal path. The insertion assistance unit 42 displays distance information indicating the calculated distance on the display unit 5. The distance information is included in the insertion assistance information. Distance information D120 is displayed on the image IMG 20.

In the above-described example, the path-processing unit 41 uses the shape information included in the subject information output from the external PC 8. In a case in which the present position of the distal end portion 20 is set as an origin, the path-processing unit 41 may calculate a position on a 3D shape of a subject corresponding to the present position on the basis of the amount of positional change from a reference position on the subject to the present position. For example, the reference position is the position of an entrance through which the insertion unit 2 is inserted. The path-processing unit 41 may use the calculated position as the origin. The path-processing unit 41 may calculate a posture of the distal end portion 20 at the origin on the basis of the amount of postural change of the distal end portion 20 while the distal end portion 20 moves from the reference position to the present position. For example, the posture of the distal end portion 20 at the reference position is known.

The image-processing unit 30 may generate shape information including a position and a posture calculated through the localization. The path-processing unit 41 may acquire the shape information from the image-processing unit 30 in Step SAL. The path-processing unit 41 may calculate an optimal path in Step SB by using the shape information. In a case in which the present position of the distal end portion 20 is set as an origin, the origin is associated with a position on a 3D shape indicated by the shape information. The posture of the distal end portion 20 at the origin is associated with posture information included in the shape information.

The insertion assistance unit 42 displays the insertion assistance information on the display unit 5 (information-reporting device). A method of outputting the insertion assistance information is not limited to this.

An output unit of the insertion assistance unit 42 may output sound data to a speaker and may cause the speaker to generate a sound corresponding to the insertion assistance information. The insertion assistance unit 42 may output a control signal indicating a pattern of vibration to a vibration generator and may cause the vibration generator to generate a vibration having a pattern corresponding to the insertion assistance information. The insertion assistance unit 42 may output a control signal indicating a pattern of light emission to a light source and may cause the light source to generate light having a pattern corresponding to the insertion assistance information.

An insertion assistance method according to each aspect of the present invention assists the insertion operation of the insertion unit 2 including the distal end portion 20 that acquires an optical image of a subject when the insertion unit 2 is inserted into the subject. The insertion assistance method includes a setting step, a state estimation step, a path calculation step, a state determination step, and an insertion assistance step. The setting unit 410 sets a first position (destination) and a second position (origin) in the shape information in the setting step (Step SB200 and Step SB201). The shape information indicates a 3D shape of the subject. The first position indicates a target position. The second position is different from the first position. The target state estimation unit 411 estimates a first state of the distal end portion 20 at the first position on the basis of a specification of the insertion unit 2 in the state estimation step (Step SB1). The path calculation unit 412 calculates a path through which the distal end portion 20 passes when the distal end portion 20 moves from the second position to the first position in the path calculation step (Step SB2). The state determination unit 40 determines a second state of the distal end portion 20 at the second position in the state determination step (Step SA3). The insertion assistance unit 42 outputs, to the display unit 5 (information-reporting device), insertion assistance information required for the insertion operation for causing the distal end portion 20 to reach the first position from the second position through the above-described path and causing a state of the distal end portion 20 to change from the second state to the first state in the insertion assistance step (Step SC).

Each aspect of the present invention may include the following modified example. In a case in which the 3D shape of the subject includes a branch portion, the path calculation unit 412 moves the distal end portion 20 disposed at the first position (destination) in the first state to the second position (origin) in the 3D shape (Step SB202). The path calculation unit 412 records the branch portion through which the distal end portion 20 passes while the distal end portion 20 moves from the first position to the second position (Step SB203). The path calculation unit 412 calculates two or more path candidates including a path candidate passing through the branch portion (Step SB207) and selects one of the two or more path candidates as the above-described path (optimal path) (Step SB305).

Each aspect of the present invention may include the following modified example. In a case in which the 3D shape of the subject includes a branch portion, the path calculation unit 412 calculates two or more path candidates including a path candidate passing through the branch portion (Step SB207). The path calculation unit 412 analyzes the two or more path candidates in accordance with one or more indices related to at least one of the insertion unit 2 and the subject (Step SB300, Step SB301, and Step SB302). The path calculation unit 412 selects one of the two or more path candidates as the above-described path (optimal path) on the basis of an analysis result of the two or more path candidates (Step SB305).

Each aspect of the present invention may include the following modified example. The degree (weight coefficient) of importance is set for each of two or more indices in advance. The path calculation unit 412 analyzes the two or more path candidates in accordance with the two or more indices and the degree of importance (Step SB300, Step SB301, and Step SB302). The degree of importance set for each of the two or more indices is variable.

Each aspect of the present invention may include the following modified example. The path calculation unit 412 analyzes the two or more path candidates by using at least one of information indicating the size of the insertion unit 2 and information indicating the shape of the subject (Step SB300, Step SB301, and Step SB302).

Each aspect of the present invention may include the following modified example. When the insertion operation is performed, a position determination unit (the image-processing unit 30 or the position determination unit 34) determines the position of the distal end portion 20. The setting unit 410 sets the second position (origin) to the position determined by the position determination unit (Step SB200).

Each aspect of the present invention may include the following modified example. The target state estimation unit 411 estimates the first state causing the state of the distal end portion 20 at the first position (destination) to be at least one of a first observation state, a second observation state, and a third observation state (Step SB100). The first observation state (FIG. 10) is a state in which the direction of the optical axis OA10 of the observation optical system disposed in the distal end portion 20 is perpendicular to the surface of the subject. The second observation state (FIG. 11) is a state in which a predetermined direction in the distal end portion 20 matches a predetermined direction in the 3D shape of the subject. The third observation state (FIG. 12) is a state in which the distance between the distal end portion 20 and the subject is appropriate for observation of the subject.

Each aspect of the present invention may include the following modified example. The insertion operation indicates at least one of an operation of moving the insertion unit 2 in the subject, an operation of bending the insertion unit 2, and an operation of twisting the insertion unit 2.

Each aspect of the present invention may include the following modified example. The insertion assistance information includes at least one of the distance between the second position (origin) and the first position (destination), the amount of change of the direction of the distal end portion 20 to cause the direction of the distal end portion 20 to match a direction along the above-described path (optimal path), and the amount of twist to cause a twist state of the insertion unit 2 to match a twist state of the insertion unit 2 in the first state.

In the prior art, the state of the insertion unit 2 at a target position for observing an inspection portion is not considered. Therefore, even when various kinds of insertion assistance are performed and the distal end portion 20 reaches the target position, the state of the insertion unit 2 and an appearance of an image of a subject may consequently deteriorate. In addition, there is a case in which an operation of twisting or bending the insertion unit 2 is required when physical restrictions exist inside the subject. Furthermore, since characteristics related to an insertion path and physical restrictions of an endoscope are not considered, there is a case in which the insertion operation in accordance with the insertion assistance is actually difficult.

The insertion assistance unit 42 outputs, to the display unit 5, insertion assistance information required for the insertion operation of causing the state of the distal end portion 20 at the destination to be the target state. Therefore, the endoscope device 1 can assist the insertion operation of causing the state of the insertion unit 2 at the target position to be appropriate for observation of the subject.

The path calculation unit 412 can calculate a path in which the load added on the insertion unit 2 is small. Therefore, the amount of force added on the insertion unit 2 by a user in the insertion operation is reduced.

The insertion assistance unit 42 can generate the insertion assistance information to cause the posture of the distal end portion 20 including the twist state of the insertion unit 2 to be optimal. Therefore, a troublesome operation in the insertion operation is reduced. A user does not need to perform the insertion operation through trial and error at an inspection site. Therefore, work efficiency is improved. In addition, the user can easily cause the insertion unit 2 to reach an inspection portion and can perform a highly reliable inspection regardless of his/her inspection skills.

The insertion unit 2 may be inserted into a subject by using a driving device including a motor. Even in this case, by using the optimal path calculated by the path calculation unit 412, the load added on the insertion unit 2 is reduced.

First Modified Example

A first modified example of the embodiment of the present invention will be described. The optical adaptor information includes information indicating optical characteristics of the optical adaptor 7. Specifically, the optical adaptor information includes information indicating characteristics of the visual field of the optical adaptor 7. The target state estimation unit 411 disposes the distal end portion 20 at the destination in accordance with the characteristics of the visual field of the optical adaptor 7 in Step SB100.

Figure 27:
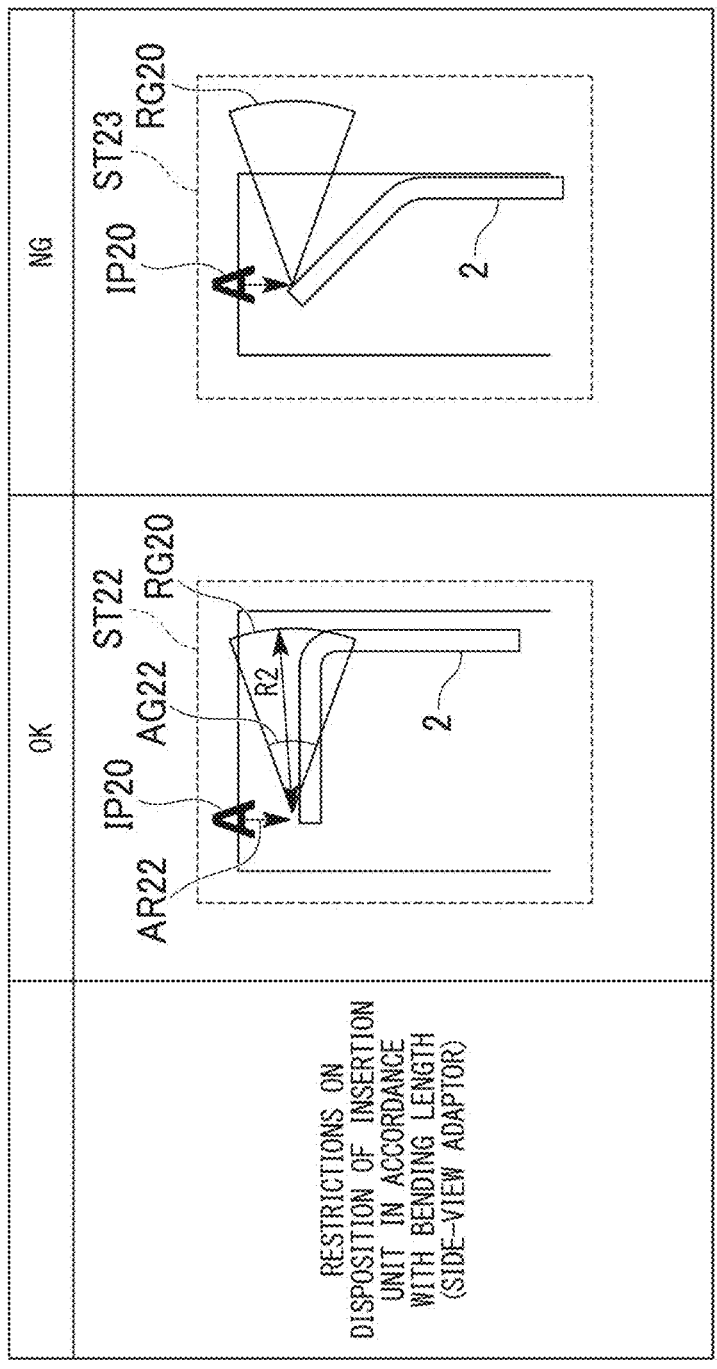
FIG. 27 is a diagram showing an example of restrictions on the disposition of the insertion unit in accordance with a bending length of the insertion unit in a first modified example of the embodiment of the present invention.
Figure 28:
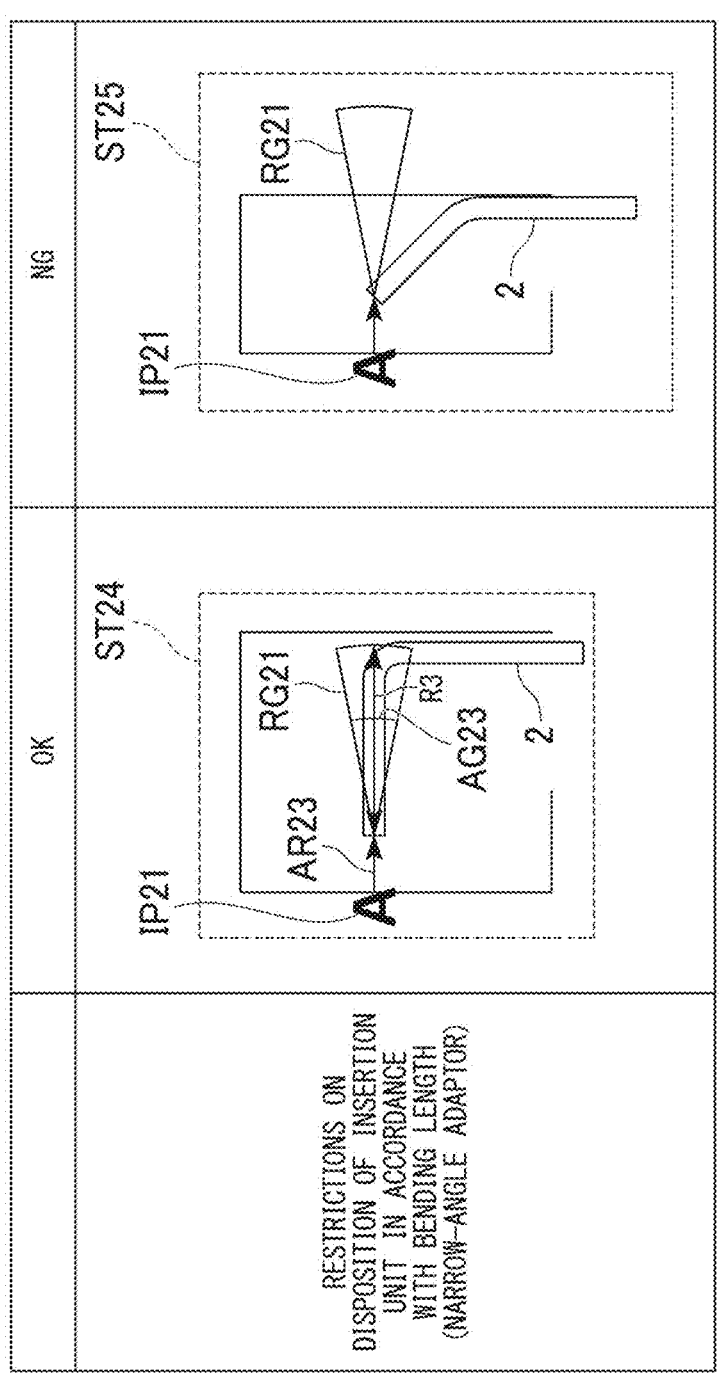
FIG. 28 is a diagram showing an example of restrictions on the disposition of the insertion unit in accordance with the bending length of the insertion unit in the first modified example of the embodiment of the present invention.
Figure 29:
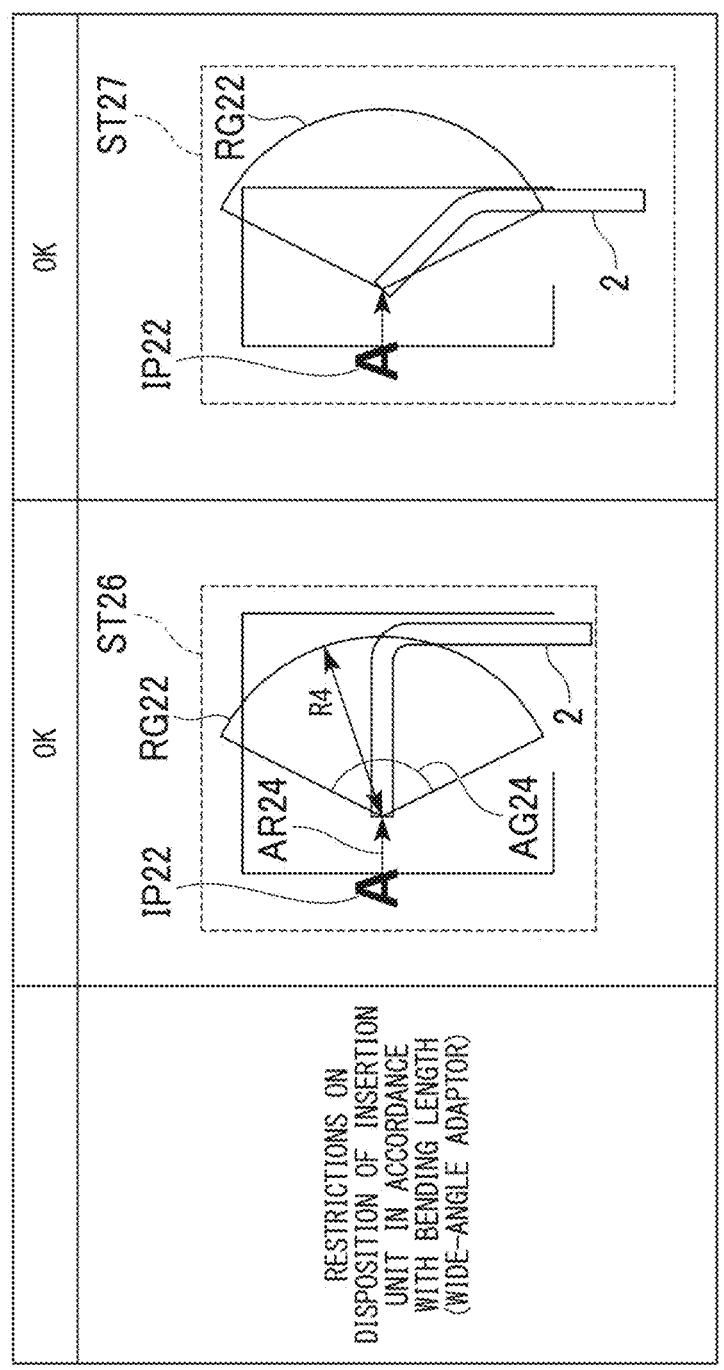
FIG. 29 is a diagram showing an example of restrictions on the disposition of the insertion unit in accordance with the bending length of the insertion unit in the first modified example of the embodiment of the present invention.

FIG. 27, FIG. 28, and FIG. 29 show examples of restrictions on the disposition of the insertion unit 2 in accordance with the bending length of the insertion unit 2. The restrictions on the disposition of the insertion unit 2 change in accordance with the characteristics of the visual field of the optical adaptor 7.

FIG. 27 shows an example of restrictions on the disposition of the insertion unit 2 related to the bending length in a case in which the optical adaptor 7 is a side-view adaptor.

The side-view adaptor acquires an optical image of a subject seen in a perpendicular direction to the side of the insertion unit 2. An arrow AR22 shown in FIG. 27 indicates the distance between an inspection portion IP20 and a necessary side-view adaptor for observation of the inspection portion IP20. The tip of the arrow AR22 indicates a target position.

A range RG20 of which reference is the position of the tip of the arrow AR22 is set. The shape of the range RG20 is a circular sector. A width R2 of the range RG20 is the same as the bending length. An angle AG22 of the range RG20 is set in accordance with the size of the visual field of the side-view adaptor.

In a state ST22 shown in FIG. 27, part of the circular arc of the range RG20 is in a space surrounded by walls of a subject. The side-view adaptor can acquire an optical image of the inspection portion IP20 in the state ST22.

In a state ST23 shown in FIG. 27, the circular arc of the range RG20 is not in the space surrounded by the walls of the subject. The side-view adaptor cannot acquire the optical image of the inspection portion IP20 in the state ST23.

The path calculation unit 412 sets the range RG20 by using the insertion unit information and the optical adaptor information. The path calculation unit 412 determines whether at least part of the circular arc of the range RG20 is in a space surrounded by walls of a subject. When the entire circular arc of the range RG20 is not in the space, the path calculation unit 412 determines that the path candidate is unavailable. When at least part of the circular arc of the range RG20 is in the space, the path calculation unit 412 determines that the path candidate is available.

FIG. 28 shows an example of restrictions on the disposition of the insertion unit 2 related to the bending length in a case in which the optical adaptor 7 is a narrow-angle adaptor. The narrow-angle adaptor has a narrow field of view. An arrow AR23 shown in FIG. 28 indicates the distance between an inspection portion IP21 and a necessary narrow-angle adaptor for observation of the inspection portion IP21. The tip of the arrow AR23 indicates a target position.

A range RG21 of which reference is the position of the tip of the arrow AR23 is set. The shape of the range RG21 is a circular sector. A width R3 of the range RG21 is the same as the bending length. An angle AG23 of the range RG21 is set in accordance with the size of the visual field of the narrow-angle adaptor.

In a state ST24 shown in FIG. 28, the circular arc of the range RG21 is in a space surrounded by walls of a subject. The narrow-angle adaptor can acquire an optical image of the inspection portion IP21 in the state ST24.

In a state ST25 shown in FIG. 28, the circular arc of the range RG21 is not in the space surrounded by the walls of the subject. The narrow-angle adaptor cannot acquire the optical image of the inspection portion IP21 in the state ST25.

The path calculation unit 412 sets the range RG21 by using the insertion unit information and the optical adaptor information. The path calculation unit 412 determines whether at least part of the circular arc of the range RG21 is in a space surrounded by walls of a subject. When the entire circular arc of the range RG21 is not in the space, the path calculation unit 412 determines that the path candidate is unavailable. When at least part of the circular arc of the range RG21 is in the space, the path calculation unit 412 determines that the path candidate is available.

FIG. 29 shows an example of restrictions on the disposition of the insertion unit 2 related to the bending length in a case in which the optical adaptor 7 is a wide-angle adaptor.

The wide-angle adaptor has a wide field of view. An arrow AR24 shown in FIG. 29 indicates the distance between an inspection portion IP22 and a necessary wide-angle adaptor for observation of the inspection portion IP22. The tip of the arrow AR24 indicates a target position.

A range RG22 of which reference is the position of the tip of the arrow AR24 is set. The shape of the range RG22 is a circular sector. A width R4 of the range RG22 is the same as the bending length. An angle AG24 of the range RG22 is set in accordance with the size of the visual field of the wide-angle adaptor.

In a state ST26 shown in FIG. 29, part of the circular arc of the range RG22 is in a space surrounded by walls of a subject. The wide-angle adaptor can acquire an optical image of the inspection portion IP22 in the state ST26.

In a state ST27 shown in FIG. 29, part of the circular arc of the range RG22 is in the space surrounded by the walls of the subject. The wide-angle adaptor can acquire an optical image of the inspection portion IP22 in the state ST27.

In a case in which the wide-angle adaptor is used, a state in which a subject is observed in a diagonal direction is likely to be allowed. Even when the width of a space in the subject is small and a bending angle is small, the wide-angle adaptor can acquire an optical image of the subject.

The path calculation unit 412 sets the range RG22 by using the insertion unit information and the optical adaptor information. The path calculation unit 412 determines whether at least part of the circular arc of the range RG22 is in a space surrounded by walls of a subject. When the entire circular arc of the range RG22 is not in the space, the path calculation unit 412 determines that the path candidate is unavailable. When at least part of the circular arc of the range RG22 is in the space, the path calculation unit 412 determines that the path candidate is available.

The optical adaptor 7 may be configured to be an optical adaptor that can switch between a direct-view state and a side-view state. In a case in which such an optical adaptor is used, the path calculation unit 412 can calculate a path candidate for which the influence of the path length is reduced.

The image-processing unit 30 may have an image rotation function. The insertion assistance unit 42 may determine whether the image rotation function is set in the image-processing unit 30 on the basis of the device-setting information. When the insertion assistance unit 42 determines that the image rotation function is set in the image-processing unit 30, Step SC1 and Step SC2 shown in FIG. 23 do not need to be executed.

Each aspect of the present invention may include the following modified example. The path calculation unit 412 calculates a path (optimal path) on the basis of a specification of the optical adaptor 7 mounted on the distal end portion 20.

The path calculation unit 412 can analyze restrictions on the disposition of the insertion unit 2 on the basis of the optical characteristics of the optical adaptor 7. The insertion assistance unit 42 can determine whether to assist an operation of twisting the insertion unit 2 on the basis of the setting of the image rotation function.

(Second modified example) A second modified example of the embodiment of the present invention will be described. The insertion assistance information in the second modified example includes an insertion history of the insertion unit 2.

The insertion assistance unit 42 records the position of the distal end portion 20 determined by the state determination unit 40 on the memory 43. The insertion assistance unit 42 generates an image of a 3D shape of a subject on the basis of the shape information included in the subject information. In addition, the insertion assistance unit 42 reads one or more positions of the distal end portion 20 recorded on the memory 43. The insertion assistance unit 42 superimposes the one or more positions on the image of the 3D shape. The insertion assistance unit 42 outputs the image to the display unit 5 via the image-processing unit 30.

Figure 30:
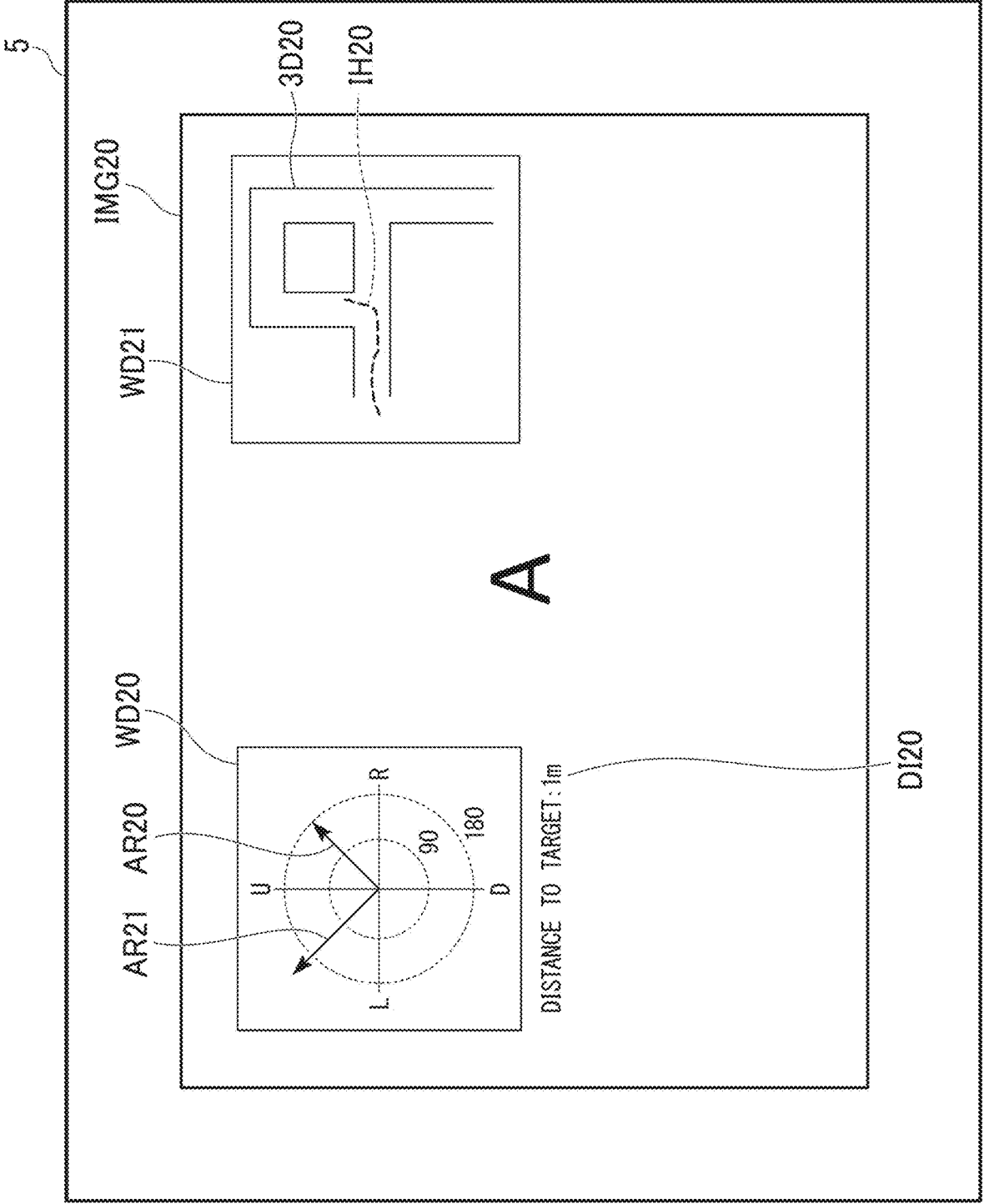
FIG. 30 is a diagram showing an example of insertion assistance information displayed on a display unit in a second modified example of the embodiment of the present invention.

FIG. 30 shows an example of the insertion assistance information displayed on the display unit 5. The same parts as those shown in FIG. 26 will not be described.

A window WD21 is displayed on an image IMG20. A 3D shape 3D20 and an insertion history IH20 are displayed in the window WD21. The insertion history IH20 indicates a history of one or more positions of the distal end portion 20. The insertion history IH20 is superimposed on an image of the 3D shape 3D20. The optimal path calculated by the path calculation unit 412 may be superimposed on the image of the 3D shape 3D20.

Each aspect of the present invention may include the following modified example. The insertion assistance information includes a history of a position through which the distal end portion 20 passes.

It is effective to display an actual path from a position through which the insertion unit 2 is inserted to a present position. The path shows a present bending state of the entire insertion unit 2 and shows a position of an ascending slope or a descending slope through which the insertion unit 2 has passed. A user can determine whether a future insertion operation of the insertion unit 2 is easy.

While preferred embodiments of the invention have been described and shown above, it should be understood that these are examples of the invention and are not to be considered as limiting. Additions, omissions, substitutions, and other modifications can be made without departing from the spirit or scope of the present invention.

Accordingly, the invention is not to be considered as being limited by the foregoing description, and is only limited by the scope of the appended claims.

What is claimed is:

1. An insertion assistance system configured to assist an insertion operation of an insertion unit when the insertion unit is inserted into a subject, the insertion unit including a lens that is disposed at a distal end of the insertion unit and is configured to acquire an optical image of the subject, the insertion assistance system comprising a processor configured to:

set a first position and a second position in shape information indicating a three-dimensional shape of the subject, wherein the first position is different than a current position of the distal end and indicates a target position being a predetermined position that the distal end of the insertion unit is intended to reach, and wherein the second position is different from the first position;

calculate an estimated first state for the distal end to be in at the first position on the basis of a specification of the insertion unit, the first state including a first posture of the distal end;

calculate a path through which the distal end passes when moving from the second position to the first position and the estimated first state;

determine a second state of the distal end at the second position, the second state including a second posture of the distal end; and output, to an information-reporting device, insertion assistance information required for the insertion operation for causing the distal end to reach the first position from the second position through the path and causing a state of the distal end to change from the second state to the first state.

2. The insertion assistance system according to claim 1, wherein, in a case in which the three-dimensional shape includes a branch portion, the processor is configured to:

record the branch portion through which the distal end disposed at the first position in the first state passes while the distal end moves from the first position to the second position in the three-dimensional shape;

calculate two or more path candidates including a path candidate passing through the branch portion; and select one of the two or more path candidates as the path.

3. The insertion assistance system according to claim 1, wherein, in a case in which the three-dimensional shape includes a branch portion, the processor is configured to:

calculate two or more path candidates including a path candidate passing through the branch portion;

analyze the two or more path candidates in accordance with one or more indices related to at least one of the insertion unit and the subject; and select one of the two or more path candidates as the path on the basis of a result of analyzing the two or more path candidates.

4. The insertion assistance system according to claim 3, wherein a degree of importance is set for each of two or more indices including the one or more indices in advance, wherein the processor is configured to analyze the two or more path candidates m accordance with the two or more indices and the degree of importance, and wherein the degree of importance set for each of the two or more indices is variable.

5. The insertion assistance system according to claim 3, wherein the processor is configured to analyze the two or more path candidates by using at least one of information indicating a size of the insertion unit and information indicating a shape of the subject.

6. The insertion assistance system according to claim 1, wherein, when the insertion operation is performed, the processor is configured to:

determine a position of the distal end; and set the second position to the determined position.

7. The insertion assistance system according to claim 1, wherein the processor is configured to estimate the first state causing a state of the distal end at the first position to be at least one of a first observation state, a second observation state, and a third observation state, wherein the first observation state is a state in which a direction of an optical axis of the lens is perpendicular to a surf ace of the subject, wherein the second observation state is a state in which a predetermined direction in the distal end matches a predetermined direction in the three-dimensional shape, and wherein the third observation state is a state in which a distance between the distal end and the subject is appropriate for observation of the subject.

8. The insertion assistance system according to claim 1, wherein the insertion operation indicates at least one of an operation of moving the insertion unit in the subject, an operation of bending the insertion unit, and an operation of twisting the insertion unit.

9. The insertion assistance system according to claim 1, wherein the insertion assistance information includes at least one of a distance between the second position and the first position, an amount of change of a direction of the distal end to cause the direction of the distal end to match a direction along the path, and an amount of twist to cause a twist state of the insertion unit to match a twist state of the insertion unit in the first state.

10. The insertion assistance system according to claim 1, wherein the insertion assistance information includes a history of a position through which the distal end passes.

11. The insertion assistance system according to claim 1, wherein the processor is configured to calculate the path on the basis of a specification of an optical adaptor mounted on the distal end.

12. An insertion assistance method causing a processor to assist an insertion operation of an insertion unit when the insertion unit is inserted into a subject, the insertion unit including a lens that is disposed at a distal end of the insertion unit and is configured to acquire an optical image of the subject, the insertion assistance method comprising:

setting a first position and a second position in shape information indicating a three-dimensional shape of the subject, wherein the first position is different than a current position of the distal end and indicates a target position being a position that the distal end of the insertion unit is intended to reach, and wherein the second position is different from the first position;

estimating a first state of the distal end at the first position on the basis of a specification of the insertion unit, the first state including a first posture of the distal end;

calculating a path through which the distal end passes when moving from the second position to the first position and the estimated first state by using the processor;

determining a second state for the distal end to be in at the second position, the second state including a second posture of the distal end; and outputting, to an information-reporting device, insertion assistance information required for the insertion operation for causing the distal end to reach the first position from the second position through the path and causing a state of the distal end to change from the second state to the first state.

13. A non-transitory computer-readable recording medium storing a program causing a computer to execute processing of assisting an insertion operation of an insertion unit when the insertion unit is inserted into a subject, the insertion unit including a lens that is disposed at a distal end of the insertion unit and is configured to acquire an optical image of the subject, the processing comprising:

setting a first position and a second position in shape information indicating a three-dimensional shape of the subject, wherein the first position is different than a current position of the distal end and indicates a target position being a position that the distal end of the insertion unit is intended to reach, and wherein the second position is different from the first position;

estimating a first state for the distal end to be in at the first position on the basis of a specification of the insertion unit, the first state including a first posture of the distal end;

calculating a path through which the distal end passes when moving from the second position to the first position and the estimated first state;

determining a second state of the distal end at the second position, the second state including a second posture of the distal end; and outputting, to an information-reporting device, insertion assistance information required for the insertion operation for causing the distal end to reach the first position from the second position through the path and causing a state of the distal end to change from the second state to the first state.

* * * * *